United States Patent
Tateishi et al.

(10) Patent No.: US 9,700,270 B2
(45) Date of Patent: Jul. 11, 2017

(54) RADIATION IMAGING DEVICE

(71) Applicant: FUJIFILM Corporation, Tokyo (JP)

(72) Inventors: Masateru Tateishi, Ashigarakami-gun (JP); Takeyasu Kobayashi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/920,093

(22) Filed: Oct. 22, 2015

(65) Prior Publication Data

US 2016/0135766 A1    May 19, 2016

(30) Foreign Application Priority Data

Nov. 19, 2014 (JP) .................................. 2014-234654
Sep. 2, 2015 (JP) .................................. 2015-173140

(51) Int. Cl.
*H01L 27/146* (2006.01)
*A61B 6/00* (2006.01)

(52) U.S. Cl.
CPC .............. *A61B 6/44* (2013.01); *A61B 6/4266* (2013.01); *A61B 6/4429* (2013.01); *A61B 6/5241* (2013.01)

(58) Field of Classification Search
CPC ..... G01T 1/2014; G01T 1/2018; G01T 1/244; G01T 7/00; G01T 1/24
See application file for complete search history.

(56) References Cited

U.S. PATENT DOCUMENTS

| 3,774,045 | A | | 11/1973 | Trott |
| 4,057,733 | A | * | 11/1977 | Hofmockel .............. A61B 6/08 378/170 |
| 5,954,469 | A | | 9/1999 | Ngo et al. |
| 6,059,454 | A | * | 5/2000 | Masson ................ A61B 6/0421 378/177 |
| 6,273,606 | B1 | | 8/2001 | Dewaele et al. |
| 2004/0071269 | A1 | * | 4/2004 | Wang .................... G06T 3/0075 378/174 |

(Continued)

FOREIGN PATENT DOCUMENTS

| JP | 2002-085392 A | 3/2002 |
| JP | 2009-237074 A | 10/2009 |

(Continued)

OTHER PUBLICATIONS

Communication dated Apr. 19, 2016 from Japanese Patent Office issued in counterpart application No. 15189824.4.

(Continued)

*Primary Examiner* — Kiho Kim
(74) *Attorney, Agent, or Firm* — Sughrue Mion, PLLC

(57) ABSTRACT

Disclosed is a radiation imaging device with excellent user-friendliness even in a comparatively large device configuration. A radiation imaging device includes radiation detectors and a housing. The radiation imaging device includes a plurality of radiation detectors, each of which has a detection surface for detecting a radiation image. The housing includes a top plate, and a frame body which is a sidewall provided at the edge of the top plate, a recess portion being provided in the frame body, and accommodates a plurality of radiation detectors in a state where the detection surfaces are aligned in a direction along the surface of the top plate.

22 Claims, 18 Drawing Sheets

(56) References Cited

U.S. PATENT DOCUMENTS

| | | | |
|---|---|---|---|
| 2004/0200971 A1* | 10/2004 | De Keyser | A61B 6/00 250/370.09 |
| 2005/0276383 A1 | 12/2005 | Bertram et al. | |
| 2009/0028298 A1* | 1/2009 | Ohta | A61B 6/4233 378/165 |
| 2011/0233415 A1 | 9/2011 | Nakatsugawa et al. | |
| 2012/0153172 A1 | 6/2012 | Sumi | |
| 2012/0219115 A1 | 8/2012 | Okada et al. | |
| 2013/0140460 A1 | 6/2013 | Kobayashi | |
| 2013/0266116 A1* | 10/2013 | Abenaim | G01N 23/046 378/20 |

FOREIGN PATENT DOCUMENTS

| | | |
|---|---|---|
| JP | 2010-259489 A | 11/2010 |
| JP | 2012-202735 A | 10/2012 |

OTHER PUBLICATIONS

Communication, dated Apr. 19, 2016, from the European Patent Office, issued in counterpart application No. 15189824.4.

* cited by examiner

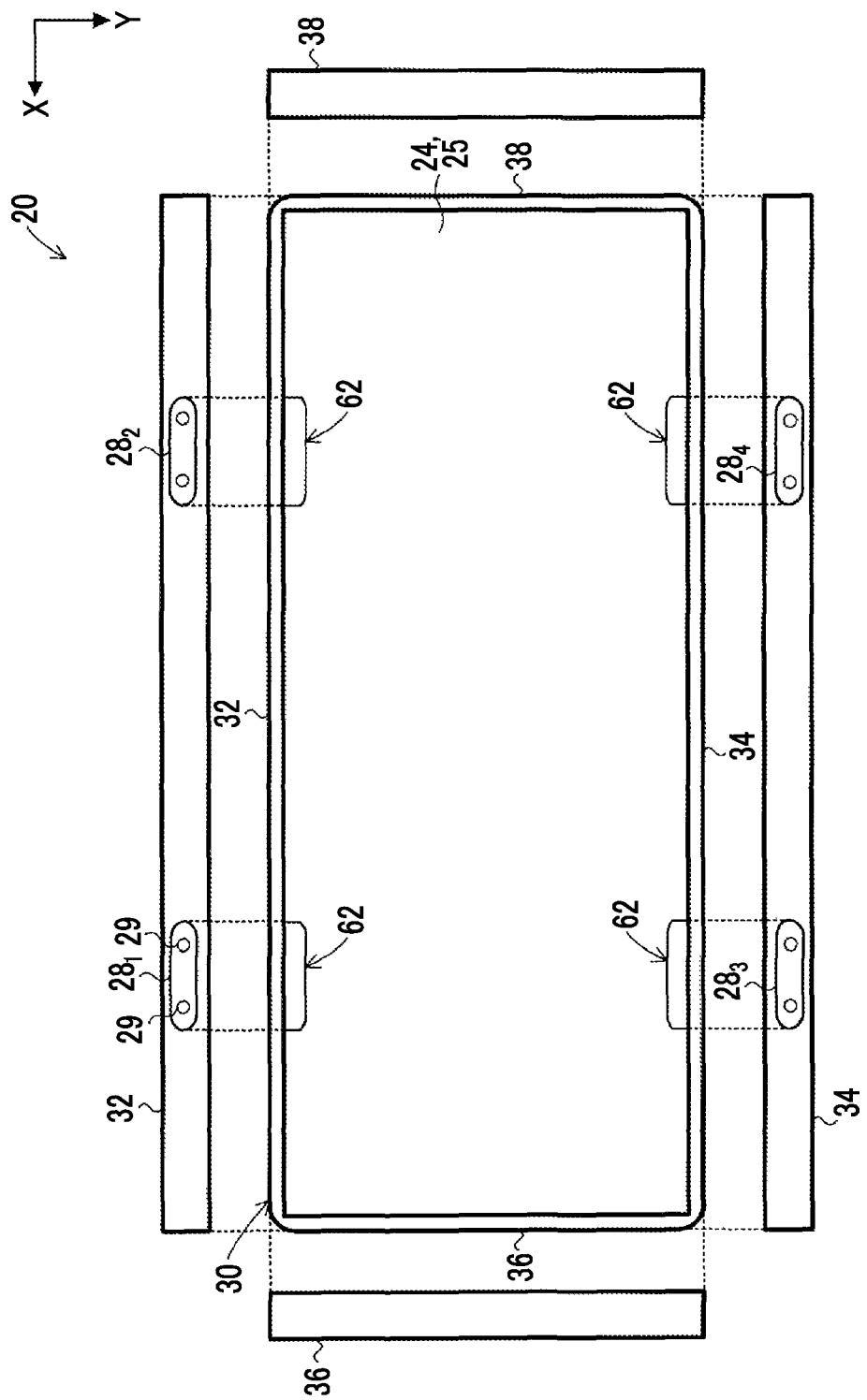

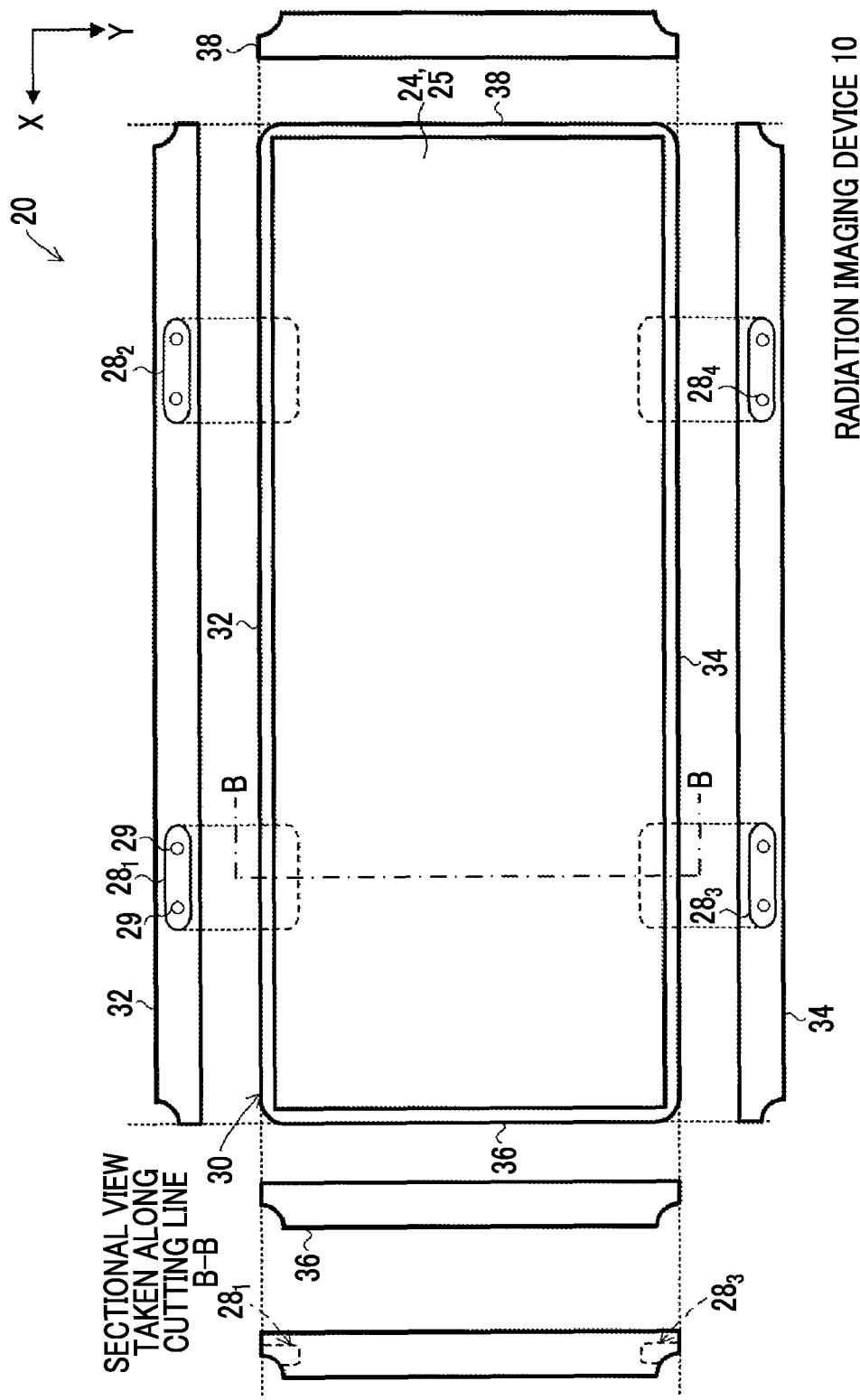

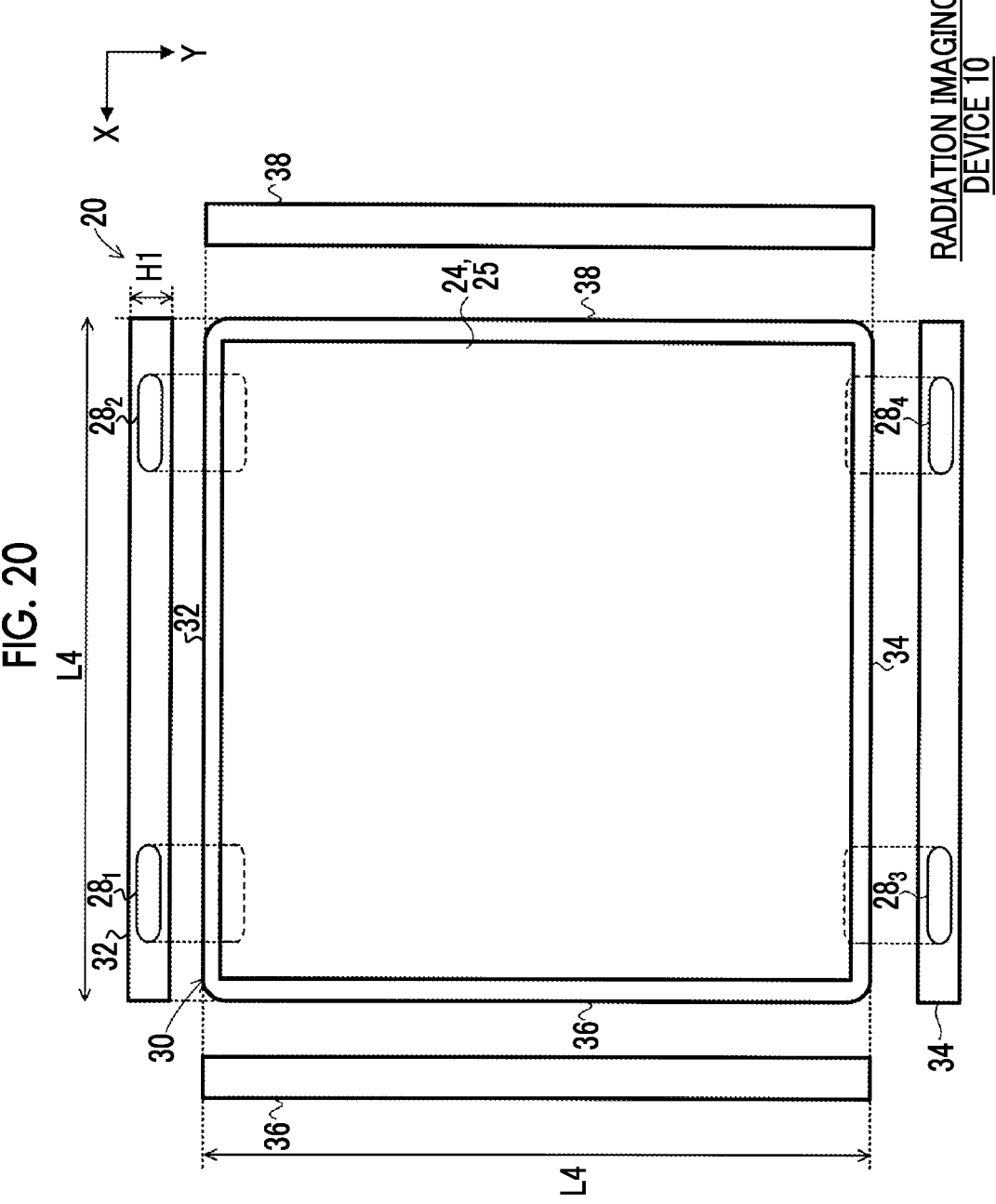

RADIATION IMAGING DEVICE

CROSS-REFERENCE TO RELATED APPLICATIONS

The present application claims priority under 35 U.S.C. §119 to Japanese Patent Application No. 2014-234654, filed on Nov. 19, 2014 and Japanese Patent Application No. 2015-173140, filed on Sep. 2, 2015. Each of the above application(s) is hereby expressly incorporated by reference, in its entirety, into the present application.

BACKGROUND OF THE INVENTION

1. Field of the Invention

The present invention relates to a radiation imaging device.

2. Description of the Related Art

Hitherto, as a radiation imaging device which images an object, for example, a radiation imaging device which performs radiography for medical diagnosis has been known. The radiation imaging device detects radiation exposed from a radiation exposure device and transmitted through an object by a radiation detector to capture a radiation image. The radiation detector generates electric charge according to exposed radiation to detect a radiation image and collects and reads the generated electric charge to capture a radiation image.

A technique which, in the case where imaging a large object, for example, an object including the chest, an abdomen, a leg, or the like of a human at one time, or the like, performs imaging by a radiation imaging device including a plurality of radiation detectors accommodated in a housing in a state where detection surfaces for detecting a radiation image are aligned has been known. For example, JP2002-85392A describes a technique which performs elongated digital imaging by an elongated radiation imaging device including a plurality of stimulable phosphor detector.

On the other hand, a technique in which, upon capturing a radiation image at a different place or on a different imaging stand, a grip (so-called handle) is provided in the housing in order to move the installation position of the radiation imaging device has been known. JP2009-237074A describes a radiation imaging device in which a grip member is provided in a housing accommodating a radiation detector.

SUMMARY OF THE INVENTION

However, in the case of moving the radiation imaging device including a plurality of radiation detectors described above, since the radiation imaging device is large and heavy compared to a radiation imaging device including a single radiation detector, there is a problem in user-friendliness.

Even in the radiation imaging device including a single radiation detector, in the case where the radiation detector is comparatively large, there is a problem in user-friendliness like the radiation imaging device including a plurality of radiation detectors.

In the case of using the radiation imaging device having a grip described above, since the grip comes into contact with an object or is obstructive in the case where the radiation imaging device is installed at a predetermined position, there is a problem in user-friendliness.

An object of the invention is to provide a radiation imaging device with excellent user-friendliness even in a comparatively large device configuration.

In order to solve the problems described above, a radiation imaging device of the invention includes a plurality of radiation detectors each of which has a detection surface for detecting a radiation image, and a housing which includes a top plate, and a sidewall provided at the edge of the top plate, a recess portion being provided in the sidewall, and accommodates the plurality of radiation detectors in a state where the detection surfaces are aligned in a direction along the surface of the top plate.

In the radiation imaging device of the invention, the radiation detectors may include a plurality of pixels, each of which includes a sensor unit configured to generate electric charge according to exposed radiation and a switch element configured to read and output the electric charge from the sensor.

In the radiation imaging device of the invention, the inside of a recess in the recess portion may be sealed.

In the radiation imaging device of the invention, a plurality of recess portions may be provided in the sidewall.

In the radiation imaging device of the invention, the top plate may have a rectangular shape, the sidewall may include a pair of sidewalls provided to face each other, and at least one recess portion may be provided in each of the pair of sidewalls.

In the radiation imaging device of the invention, the recess portions may be provided at facing positions of the pair of sidewalls.

In the radiation imaging device of the invention, the top plate may have a rectangular shape, the sidewall may include a pair of sidewalls provided at the edge of the top plate in a longitudinal direction, and the recess portions may be provided in the pair of sidewalls.

In the radiation imaging device of the invention, a pair of recess portions may be provided in each of a pair of sidewalls provided to face each other.

In the radiation imaging device of the invention, the pair of recess portions in one sidewall and the pair of recess portions in the other sidewall may be provided at positions capable of being gripped by both hands of a human.

In the radiation imaging device of the invention, the recess portions may be provided in each of a pair of sidewalls provided to face each other in an elongated shape with respect to the direction along the surface of the top plate.

In the radiation imaging device of the invention, the recess portions may be provided in an arc shape in plan view to extend from the top plate side toward an opposite side with respect to the direction along the surface of the top plate.

In the radiation imaging device of the invention, a plurality of recess portions may be provided in each of a pair of sidewalls provided to face each other with respect to the direction along the surface of the top plate.

In the radiation imaging device of the invention, the recess portions may be aligned in an arc shape in plan view to extend from the top plate side toward an opposite side with respect to the direction along the surface of the top plate.

In the radiation imaging device of the invention, the recess portion may become a fixing portion in the case where the device is fixed to an imaging stand. The term "the device" herein used refers to the radiation imaging device.

In the radiation imaging device of the invention, the recess portion may become a fixing portion in the case where an object is imaged using a grid which removes scattered radiation included in radiation transmitted through the object and the device is fixed to the grid.

In the radiation imaging device of the invention, in the case where the recess portion becomes a fixing portion and the device is fixed to an imaging stand by a screw, a screw hole into which the screw is screwed may be provided inside a recess. Instead of the screw, bolts and nuts, stud or the like can be used to fix to the imaging stand.

In the radiation imaging device of the invention, the position of the recess portion may be displayed on the top plate.

In the radiation imaging device of the invention, the size of the recess portion may be defined by the size of a gripping portion of a human in the case where the human grips the device.

In the radiation imaging device of the invention, the plurality of radiation detectors may be accommodated in the housing in a state where the end portions of adjacent radiation detectors overlap each other.

In the radiation imaging device of the invention, the plurality of radiation detectors may be formed integrally.

A radiation imaging device of the invention includes a single radiation detector which has a detection surface for detecting a radiation image, the detection surface having a size equal to or greater than a size determined in advance, and a housing which includes a top plate, and a sidewall provided at the edge of the top plate, a recess portion being provided in the sidewall, and accommodates the single radiation detector such that the detection surface faces the surface of the top plate.

According to the invention, the effect that user-friendliness of the radiation imaging device is improved even in a comparatively large device configuration is obtained.

BRIEF DESCRIPTION OF THE DRAWINGS

FIG. 18 is an example of a radiation imaging device in which a position of a recess portion is displayed on an imaging surface of a top plate.

FIG. 19 is a plan view and a side view of another example of a radiation imaging device when viewed from an exposure side of radiation R.

FIG. 20 is a plan view and a side view of another example of a radiation imaging device when viewed from an exposure side of radiation R.

DESCRIPTION OF THE PREFERRED EMBODIMENTS

Figure 1:
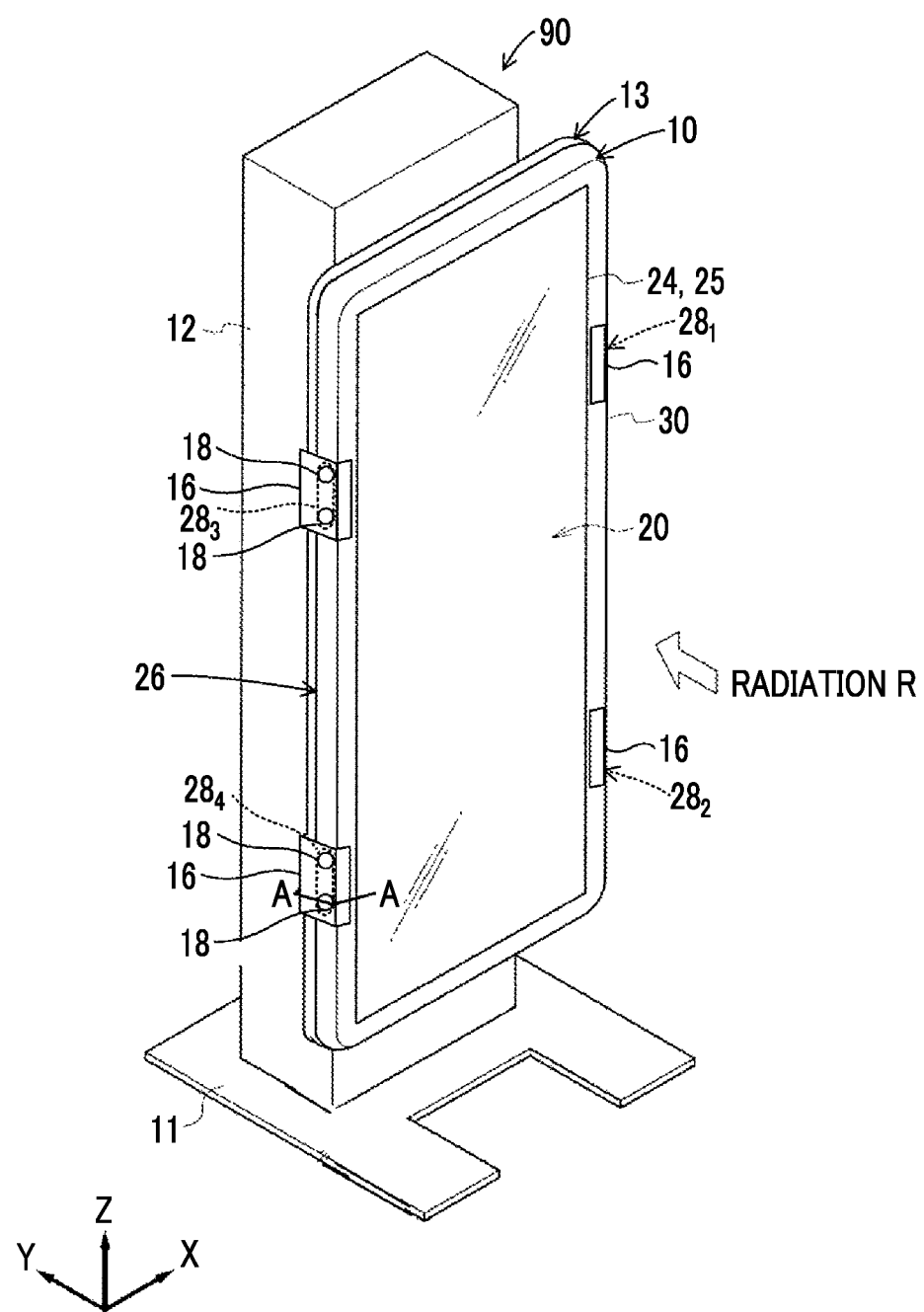
FIG. 1 is a perspective view when viewed from an exposure side of radiation R when a radiation imaging device of an embodiment is installed on a standing position stand.

Hereinafter, an embodiment of the invention will be described referring to the drawings. In the drawings, parts having the same functions are represented by the same reference numerals, and overlapping description will be appropriately omitted.

FIG. 1 is a perspective view showing a state where a radiation imaging device of this embodiment is installed on a standing position stand when viewed from an exposure side of radiation R. For example, a radiation imaging device 10 is installed on a standing position stand 90 in a standing state in the case of imaging a subject (an example of an object) in a standing state or a sitting state where the subject is sitting on a chair or a wheelchair.

In FIG. 1, an arrow X direction is a horizontal direction orthogonal to an exposure direction of radiation R. An arrow Y direction is a horizontal direction matching the exposure direction of radiation R. An arrow Z direction is a vertical direction. The arrow X direction, the arrow Y direction, and the arrow Z direction are directions matching the X-axis direction, the Y-axis direction, and the Z-axis direction in the XYZ coordinates.

As shown in FIG. 1, the radiation imaging device 10 includes a rectangular flat plate-like housing 20 in which one pair of opposite sides (in the example shown in FIG. 1, sides along the Z-axis direction) are in a longitudinal direction, and the other pair of opposite sides (in the example shown in FIG. 1, sides along the X-axis direction) are in a transverse direction. The housing 20 includes a top plate 24, back plate 26, and a frame body 30 which is a sidewall of the housing. In this embodiment, the "rectangular shape" includes a shape in which a corner portion is chamfered.

The top plate 24 is fixed to the frame body 30, and a surface on the outer side of the housing 20 becomes an imaging surface 25. The imaging surface 25 is exposed to radiation R from a radiation source of a radiation exposure device (not shown). The back plate 26 is fixed to the frame body 30 facing the top plate 24 (imaging surface 25).

Figure 2:
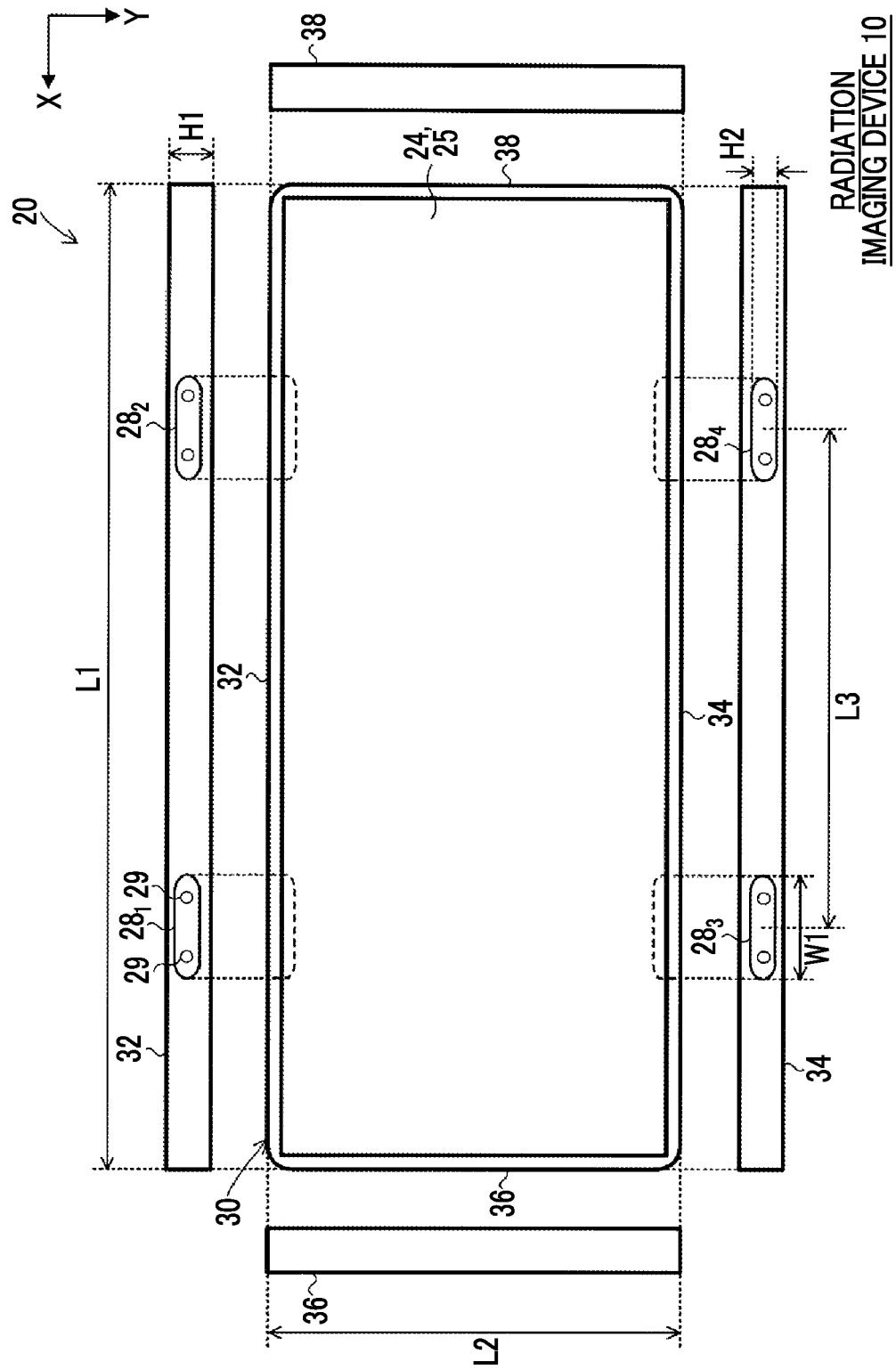
FIG. 2 is a plan view and a side view of an example of the radiation imaging device of the embodiment when viewed from an exposure side of radiation R.
Figure 3:
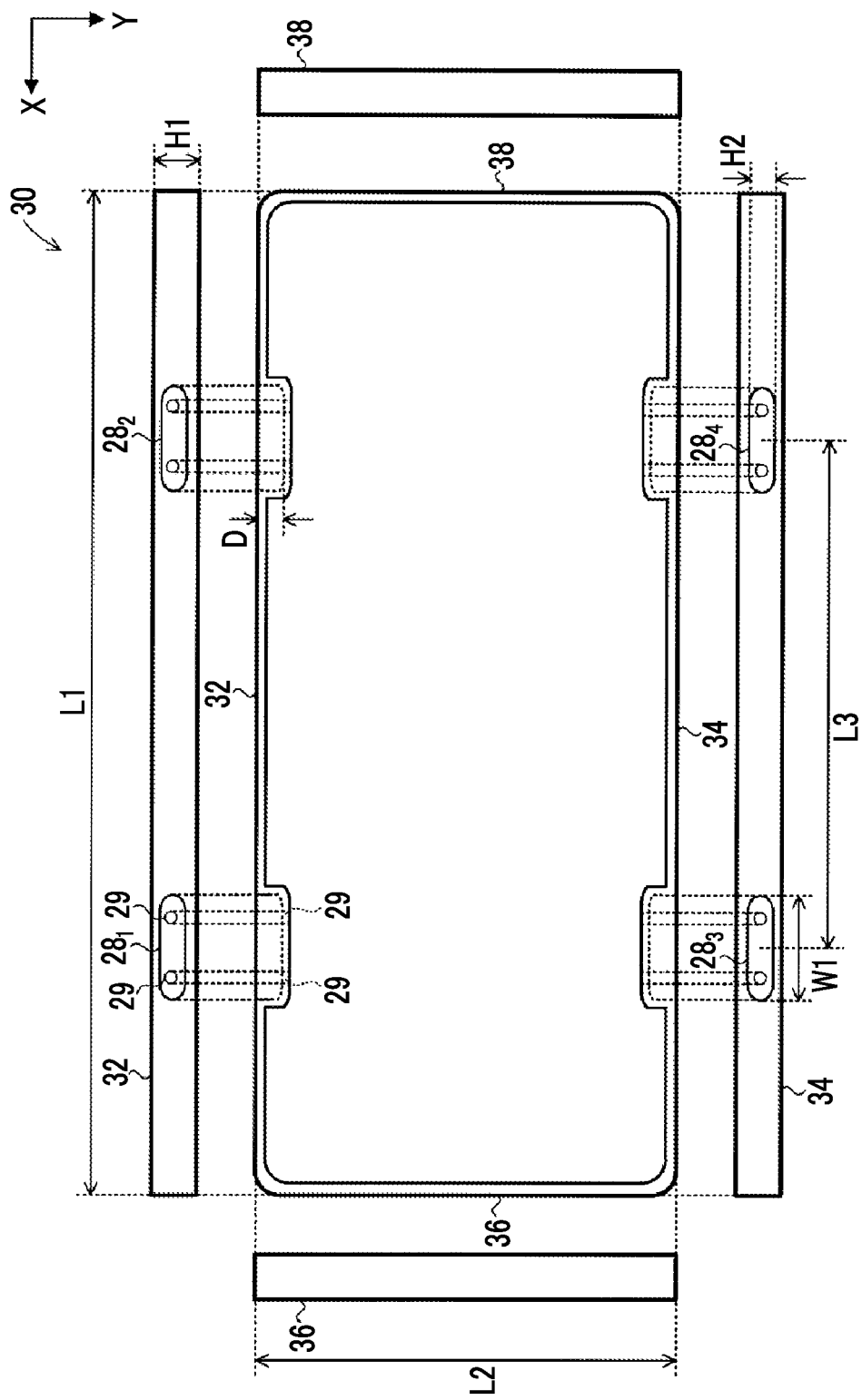
FIG. 3 is a plan view and a side view of an example of a frame body of the radiation imaging device of the embodiment when viewed from an exposure side of radiation R.

In the housing 20 of the radiation imaging device 10, the back plate 26 is in contact with an imaging stand 13, and is fixed to the imaging stand 13 by sheet metals 16 and screws 18. FIG. 2 is a plan view and a side view of an example of the radiation imaging device 10 of this embodiment when viewed from an exposure side of radiation R. FIG. 3 is a plan view and a side view of an example of the frame body 30 of the radiation imaging device 10 of this embodiment when viewed from an exposure side of radiation R. In the plan view of FIG. 2, the shape of the inside of the recess portion 28 is shown by a dotted line on the top plate 24. In FIGS. 2 and 3, the X-axis direction and the Y-axis direction in the plan view are shown. Hereinafter, in the drawings in which a plan view and a side view are shown, the X-axis direction and the Y-axis direction in the plan view are shown.

As shown in FIGS. 2 and 3, in the side surfaces of a first frame 32 and a second frame 34 which are sidewalls (hereinafter, referred to as "longitudinal sidewalls") on the longitudinal side in the frame body 30 of the housing 20, recess portions $28_1$ to $28_4$ (the details will be described below, and a plurality of recess portions are collectively referred to as "recess portions 28") having screw holes 29 (see FIG. 2 and the like) are provided. The screws 18 are screwed into the screw holes 29 of the respective recess portions 28 through the sheet metals 16.

As shown in FIG. 1, the imaging stand 13 is supported by a prismatic support column 12 in which the Z-axis direction is the longitudinal direction. A bottom plate 11 which extends outward of the support column 12 is provided in the lower end portion of the support column 12, and the imaging stand 13 and the radiation imaging device 10 are stably supported by the bottom plate 11 through the support column 12. The radiation imaging device 10 can be attached to the imaging stand 13 and can be detached from the imaging stand 13.

Figure 4:
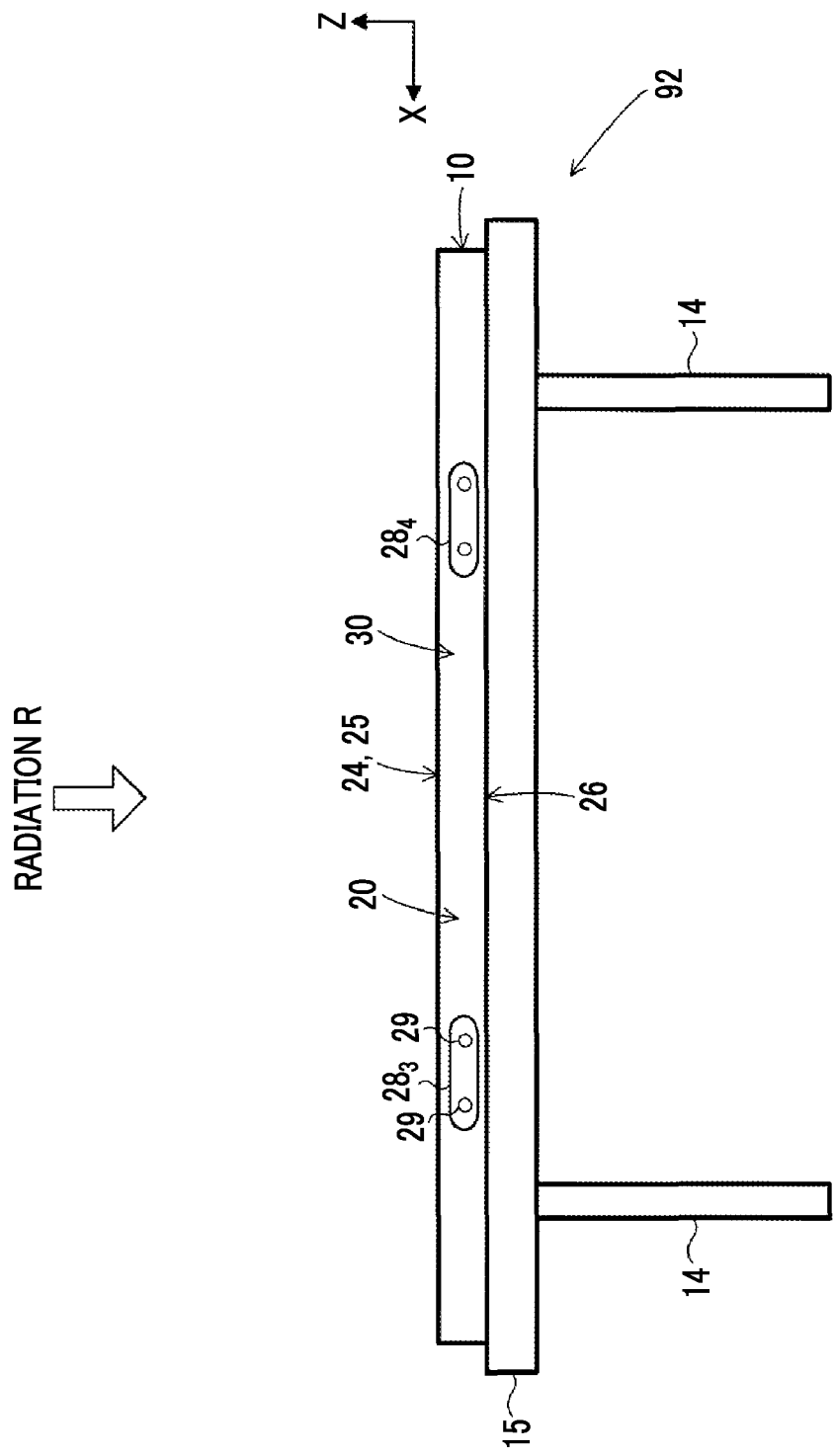
FIG. 4 is a side view when the radiation imaging device of the embodiment is installed on the lying position stand.

FIG. 4 is a side view in the case where the radiation imaging device 10 of this embodiment is installed on a lying position stand. A lying position stand 92 of this embodiment includes an imaging stand 15 on which the subject is lying on the top surface, and two support columns 14 which support the imaging stand 15. For example, in the case of imaging the subject in the lying state, as shown in FIG. 4, the radiation imaging device 10 is installed on the top surface of the imaging stand 15 of the lying position stand 92 sideways.

In this embodiment, as shown in FIG. 4, in the case of using the radiation imaging device 10 in a state of being installed on the lying position stand 92, the radiation imaging device 10 is used without being fixed to the imaging stand 15. Similarly to a case of using the radiation imaging device 10 in a state of being installed on the standing position stand 90 shown in FIG. 1, the radiation imaging device 10 may be fixed to the imaging stand 15 by the sheet metals 16 and the screws 18. The radiation imaging device 10 may be arranged directly on a bed of an imaging room, a patient's room, or the like, instead of being arranged on the imaging stand 15.

Figure 5:
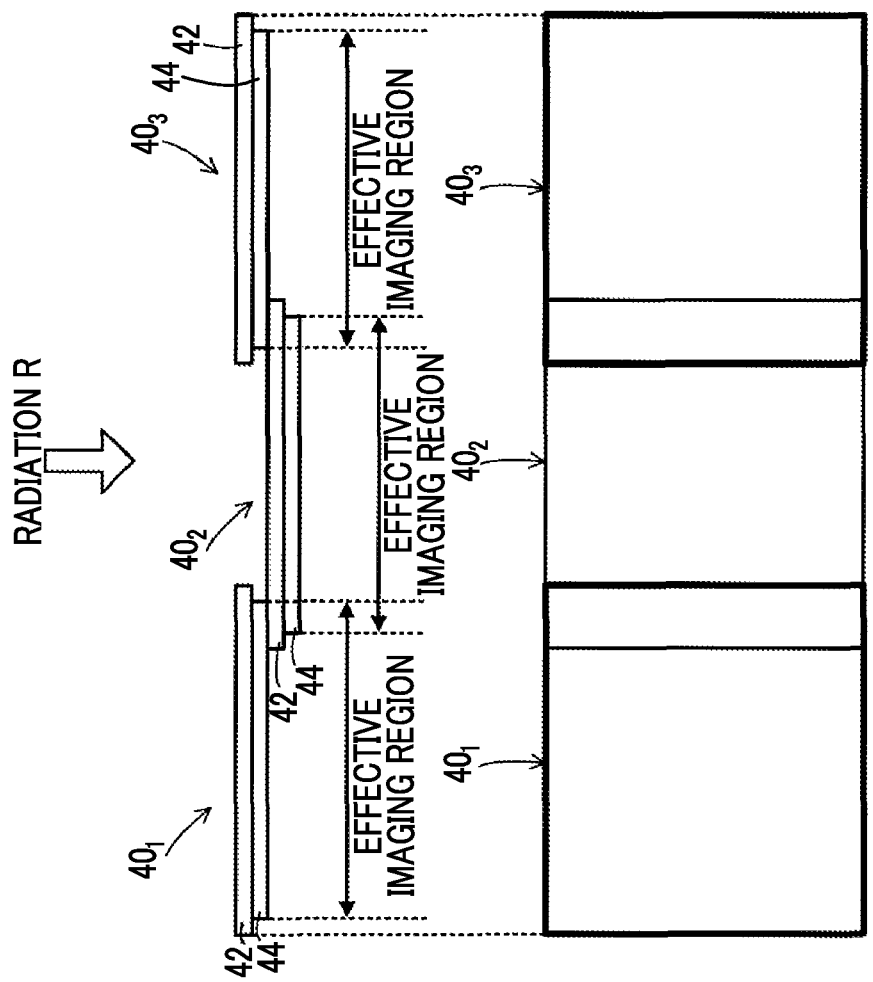
FIG. 5 is a side view and a plan view showing an example of the arrangement state of radiation detectors accommodated inside a housing of the embodiment.

The radiation imaging device 10 has a function of capturing a radiation image of the subject positioned between the radiation imaging device 10 and the radiation exposure device (not shown). FIG. 5 is a side view and a plan view showing an example of the arrangement state of radiation detectors accommodated inside the housing of this embodiment. FIG. 5 is a plan view and a side view in the case where radiation detectors are viewed from the exposure side of radiation R.

As shown in FIG. 5, the radiation imaging device 10 of this embodiment captures a radiation image by three radiation detectors $40_1$ to $40_3$ (hereinafter, collectively referred to as "radiation detectors 40"). For this reason, the three radiation detectors 40 are accommodated inside the housing 20.

As a specific example, the radiation imaging device 10 of this embodiment uses the radiation detectors 40 of an indirect conversion system, so-called digital radiography (DR), which converts radiation R to light once and converts the converted light to electric charge. Each of the radiation detectors 40 of this embodiment includes a TFT glass substrate 42 having a plurality of pixels. The plurality of pixels each including a sensor unit, which receives light, generates electric charge, and accumulates the generated electric charge, and a thin film transistor (TFT), which is a switch element for reading the accumulated electric charge in the sensor unit (all of these are not shown). In this embodiment, light converted from radiation R by a scintillator 44 is exposed, whereby electric charge is generated in the sensor unit.

Each of the radiation detectors 40 is further provided with gate wires in which a control signal for controlling the on and off of the TFT of each pixel provided on the TFT glass substrate 42 flows, and a scan signal control circuit which outputs the control signal to the gate wires (all of these are not shown). Each of the radiation detectors 40 is further provided with signal wires in which electric charge read from each pixel provided on the TFT glass substrate 42 flows, and a signal detection circuit which detects the electric charge flowing in the signal wires (all of these are not shown).

As shown in FIG. 5, in the radiation imaging device 10 of the embodiment, the three radiation detectors 40 are accommodated in the housing 20 in a state where the detection surfaces are aligned in a direction along the surface of the top plate 24. In this embodiment, the detection surface refers to a surface of the radiation detector 40 on which radiation R is detected, and specifically, refers to a surface of the TFT glass substrate 42 on the exposure side of radiation R. The radiation detectors 40 are arranged with respect to the incidence direction of radiation R in a state where the end portions of effective imaging regions (pixel regions actually contributing to capturing of a radiation image) overlap each other. Specifically, the end portion of the effective imaging region of the radiation detector $40_1$ overlaps the end portion of the effective imaging region of the radiation detector $40_2$. The end portion of the effective imaging region of the radiation detector $40_2$ overlaps the end portion of the effective imaging region of the radiation detector $40_3$. In this way, the radiation detectors 40 are arranged in a state where the end portions of the effective imaging regions overlap each other, thereby preventing defects in an elongated radiation image finally obtained. The range of the effective imaging regions overlapping each other is preferably determined in consideration of the range of the incidence angle of radiation R exposed from the radiation source of the radiation exposure device to the radiation detectors 40 (radiation imaging device 10).

As shown in FIG. 5, in the radiation imaging device 10 of this embodiment, since a radiation image is captured by the three radiation detectors 40, it is possible to capture an elongated radiation image in the entire radiation imaging device 10.

Next, the details of the housing 20 of the radiation imaging device 10 of this embodiment will be described.

As described above, the housing 20 of this embodiment includes the rectangular frame-like frame body 30 (see FIG. 3) in which the exposure side of radiation R and the opposite side are open.

As described above, the frame body 30 is provided with the top plate 24 on the exposure side of radiation R, and is provided with the back plate 26 facing the top plate 24 on the side opposite to the exposure side of radiation R. The top plate 24 of this embodiment has a rectangular flat plate shape, and is formed of a material which transmits radiation R and is lightweight. As a specific example of the top plate 24, carbon fiber reinforced plastics (CFRP) are preferably used. The back plate 26 has a rectangular flat plate shape, and is formed of, for example, the same material as the frame body 30, carbon fiber reinforced plastics, or the like.

The frame body 30 is formed by assembling a pair of a first frame 32 and a second frame 34 facing each other, and a pair of a third frame 36 and a fourth frame 38 facing each other. A pair of the first frame 32 and the second frame 34 are provided in parallel as a part of the longitudinal sidewalls described above. The first frame 32 and the second frame 34 have a length allowing the three radiation detectors 40 to be accommodated. A pair of the third frame 36 and the fourth frame 38 are provided in parallel as a part of transverse sidewalls. The third frame 36 and the fourth frame 38 have a length allowing one radiation detector 40 to be accommodated.

In the radiation imaging device 10 of this embodiment, the length L1 of the first frame 32 and the second frame 34 is 1340 mm, and the length L2 of the third frame 36 and the fourth frame 38 is 570 mm. Taking elongated imaging into consideration, the length L1 is preferably about 600 to 1600 mm, and the length L2 is preferably about 400 to 600 mm. In the radiation imaging device 10 of the embodiment, the thickness H1 of the frame body 30 which becomes the thickness of the radiation imaging device 10 is 50 mm.

The frame body 30 is formed of a material which is excellent in processability and is lightweight, for example, a light metal material, a light alloy material, or carbon fiber reinforced plastics. As the light metal material, for example, aluminum is preferably used. As the light alloy material, for example, an aluminum alloy or a magnesium alloy is preferably used.

As described above, the frame body 30 of this embodiment includes the recess portions $28_1$ to $28_4$. Specifically, as shown in FIGS. 2 and 3, the first frame 32 is provided with two recess portions $28_1$ and $28_2$, and the second frame 34 is provided with two recess portions $28_3$ and $28_4$. The recess portion $28_1$ and the recess portion $28_3$ are provided at positions facing each other. The recess portions $28_2$ and the recess portion $28_4$ are provided at positions facing each other. In the recess portions 28 of this embodiment, the inside of a recess is sealed. In the frame body 30 of this embodiment, through holes which pass therethrough are not provided, and the entire housing 20 is sealed.

The recess portions 28 of the radiation imaging device 10 of this embodiment have a shape and size allowing a finger of a human to be inserted from the outside. Specifically, in the case of moving the radiation imaging device 10, a user who wants to move the radiation imaging device 10 can insert gripping portions (only the fingers, portions including at least a part of the fingers and the palm, or the like) into the recess portion 28 to grip and lift or move the radiation imaging device 10. Specifically, in the radiation imaging device 10 of this embodiment, it is assumed that the radiation imaging device 10 is moved by two users of a first user who grips the first frame 32 side and a second user who grips the second frame 34 side. For this reason, the first frame 32 is provided with the two recess portions $28_1$ and $28_2$ corresponding to both hands of the first user, and the second frame 34 is provided with the two recess portions $28_3$ and $28_4$ corresponding to both hands of the second user.

The "moving" of the radiation imaging device 10 in this embodiment includes a case of changing the arrangement state of the radiation imaging device 10 (for example, a state of being installed on the standing position stand 90, a state of being installed on the lying position stand 92, or the like), in addition to changing a place where the radiation imaging device 10 is arranged.

For this reason, the size and the arrangement position of each of the recess portions 28 is set in consideration of the user easily moving the radiation imaging device 10, specifically, easily lifting or carrying the radiation imaging device 10. For example, the size of each of the recess portion 28 is defined by the size of each of the gripping portions (only the fingers, portions including at least a part of the fingers and the palm of the human body, or the like). For example, it is preferable that, in the case where an articulated test finger defined in Japanese Industrial Standard JIS C 0920 is used, the size of each of the recess portions 28 is set to a size allowing the test finger to be sufficiently inserted, for example, a size allowing the first knuckle of the test finger to be inserted. As a specific example, in this embodiment, the size of the recess portion 28 is set to have a width W1 equal to or greater than 80 mm and a length H2 in the thickness direction of the housing 20 equal to or greater than 15 mm.

In general, in the case where the radiation detector 40 is DR, the thickness in the exposure direction of radiation is large compared to a radiation detector which is referred to as so-called computed radiography (CR). For this reason, in the radiation imaging device 10 using DR as the radiation detector 40, the thickness H1 of the radiation imaging device 10 (the thickness of the frame body 30) is large compared to a case where the radiation detector is CR. In the radiation imaging device 10, since the end portions of the three radiation detectors 40 overlap each other, the thickness is large compared to a case where one radiation detector 40 is provided. For this reason, the radiation imaging device 10 has a thickness allowing the recess portions 28 of appropriate dimension to be provided in the frame body 30.

It is preferable that the depth D (the length in a direction along the surfaces of the third frame 36 and the fourth frame 38) of the recess portions 28 is set to a length allowing the gripping portions (only the fingers, portions including at least a part of the fingers and the palm, or the like) of a human having a length appropriate for gripping the radiation imaging device 10 to be inserted. In general, in the case where the radiation imaging device 10 is heavy, in many cases, if the fingers or the palm may be inserted deeply inside the recess portion 28, the radiation imaging device 10 is easily gripped. For this reason, the depth of the recess portions 28 may be set according to the weight or the size of the radiation imaging device 10.

For example, in regard to the positions where the recess portions 28 are arranged, in the case of assuming that the right and left hands of a human are respectively inserted into the recess portions 28, the interval L3 between the centers of a pair of recess portions 28 provided in each of the first frame 32 and the second frame 34 is set in consideration of the shoulder width of an adult man of a standard type. As a specific example, in this embodiment, the interval L3 between the centers of the pair of recess portions 28 is equal to or greater than 200 mm and equal to or less than 1100 mm.

As shown in FIG. 1, the recess portions 28 of this embodiment are used as fixing portions for fixing the radiation imaging device 10 to the imaging stand 13. For this reason, a predetermined number of (in this embodiment, two) screw holes 29 are provided inside the recess portions 28. In this embodiment, the radiation imaging device 10 is fixed to the imaging stand 13 using four recess portions 28. In the frame body 30 of this embodiment, the deepest portions of the screw holes 29 provided in the recess portions 28 are sealed, and the inside of the screw holes 29 is sealed.

Figure 6:
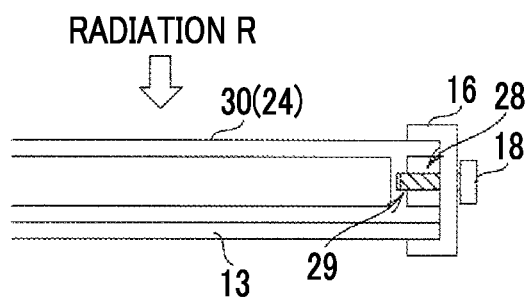
FIG. 6 is a sectional view of a fixing portion of the radiation imaging device of the embodiment taken along a cutting line A-A in FIG. 1.

As described above, the radiation imaging device 10 of this embodiment is fixed to the imaging stand 13 by the sheet metals 16 and the screws 18 which are an example of fixing members. FIG. 6 is a sectional view of a fixed portion of the radiation imaging device 10 of this embodiment taken along the cutting line A-A in FIG. 1.

The sheet metals 16 have a rectangular shape in which the end portion of each of a pair of opposite sides is bent at about 90° in the same direction. As shown in FIG. 6, the screw portions of the screws 18 are screwed into the screw holes 29 of the recess portions 28, and the top plate 24 of the frame body 30 and the imaging stand 13 are sandwiched by the sheet metals 16, whereby the radiation imaging device 10 is fixed to the imaging stand 13.

Figure 7:
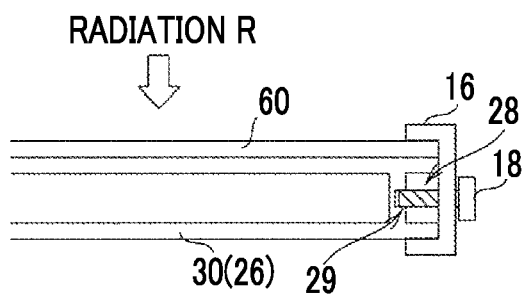
FIG. 7 is a sectional view showing a state where the radiation imaging device and a grid are fixed using a recess portion and corresponding to FIG. 6.

In this embodiment, as shown in FIG. 1, although a case where the radiation imaging device 10 is fixed to the imaging stand 13 of the standing position stand 90 using the recess portions 28 has been described, the radiation imaging device 10 can be fixed to the imaging stand 15 of the lying position stand 92 in the same manner. The invention is not limited to a case of fixing the radiation imaging device 10 to the imaging stand 13, and for example, the recess portions 28 may be used in the case of integrally fixing the radiation imaging device 10 and the grid. FIG. 7 is a sectional view showing a state where the radiation imaging device 10 and the grid are fixed using the recess portions 28, and corresponding to FIG. 6. In general, since radiation R transmitted through the subject includes scattered radiation, a grid 60 for removing scattered radiation is arranged between the subject and the radiation imaging device 10 (radiation detector 40) and a radiation image is captured. In this way, in the case where imaging is performed using the grid 60, the recess portions 28 may be used in order to integrally fix the grid 60 and the radiation imaging device 10. In this case, as an example, as shown in FIG. 7, similarly to a case of fixing the radiation imaging device 10 to the imaging stand 13, the screw portions of the screws 18 are screwed into the screw holes 29 of the recess portions 28, and the back plate 26 of the frame body 30 and the grid 60 are sandwiched by the sheet metals 16, whereby the radiation imaging device 10 and the grid 60 are integrally fixed.

Figure 8:
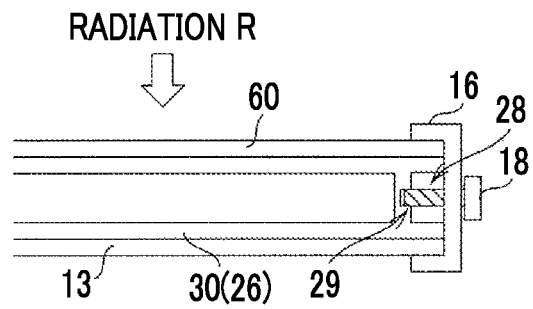
FIG. 8 is a sectional view showing a state where the radiation imaging device, an imaging stand, and a grid are fixed using a recess portion and corresponding to FIG. 6.

As shown in FIG. 8, it is needless to say that the radiation imaging device 10 and the grid 60 may be fixed to the imaging stand 13 using the recess portions 28.

The recess portions 28 provided in the housing 20 (frame body 30) are not limited to those shown in FIGS. 1 to 8 described above. Hereinafter, modification examples of the recess portions 28 will be described.

Modification Example 1

Figure 9:
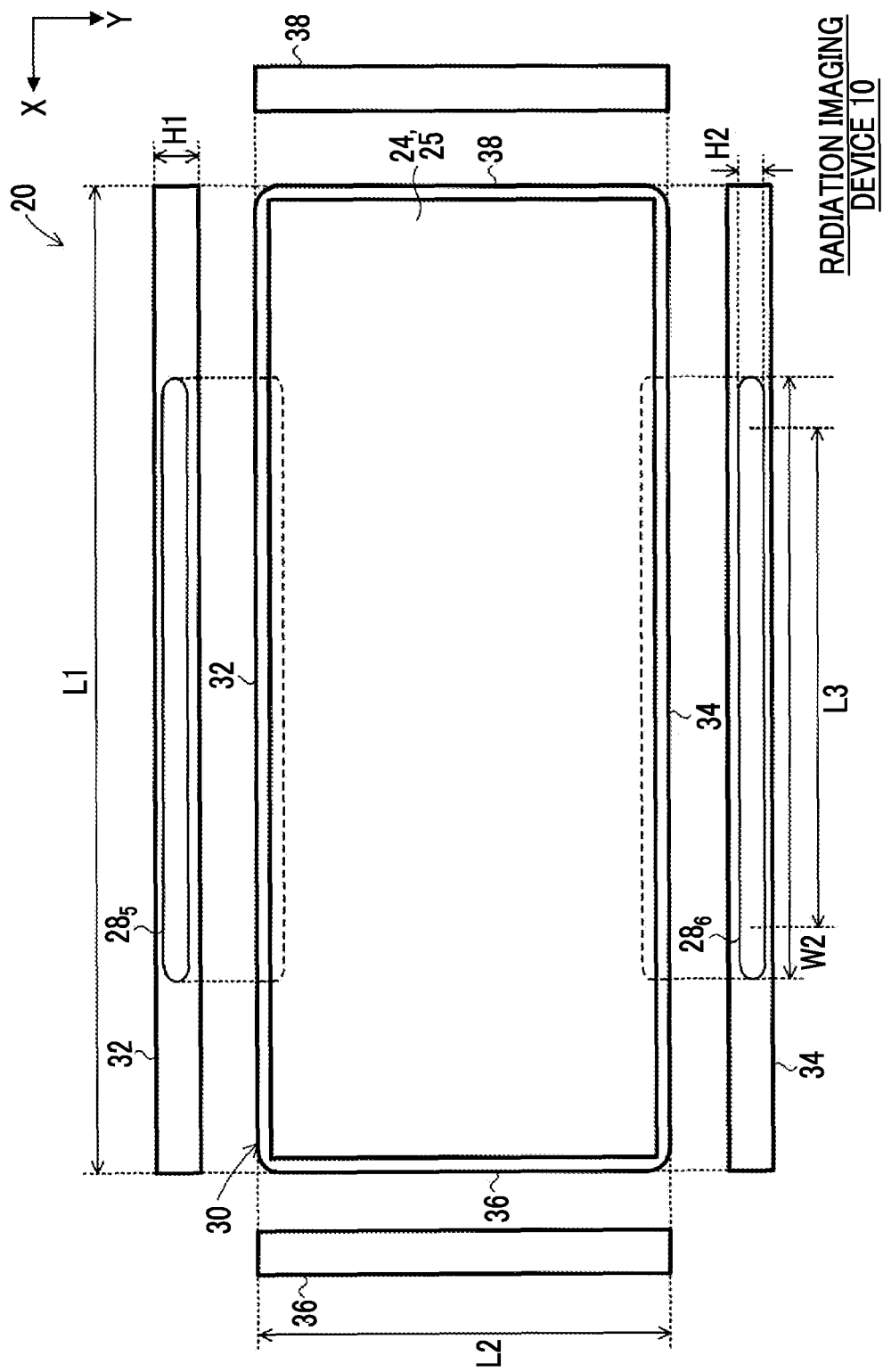
FIG. 9 is a plan view and a side view of an example of a radiation imaging device of Modification Example 1 when viewed from an exposure side of radiation R.

FIG. 9 is a plan view and a side view of an example of a radiation imaging device of this modification example when viewed from an exposure side of radiation R. In FIG. 9, the screw holes 29 are not shown.

In a radiation imaging device 10 of this modification example, in each of the first frame 32 and the second frame 34, the width W2 of the recess portions 28 is long compared to the embodiment described above such that the radiation imaging device 10 can be gripped at any positions.

As shown in FIG. 9, in the radiation imaging device 10 of this modification example, two elongated recess portions $28_5$ and $28_6$ are provided. Specifically, the first frame 32 is provided with the recess portion $28_5$, and the second frame 34 is provided with the recess portion $28_6$. The recess portion $28_5$ and the recess portion $28_6$ are provided at positions facing each other.

The width W2 of the recess portions $28_5$ and $28_6$ is longer than the width W1 of the recess portions $28_1$ to $28_4$ of the embodiment described above. It is preferable that the width W2 is equal to or greater than the interval L3 described above. As a specific example, it is preferable that the width W2 of the recess portions $28_5$ and $28_6$ is equal to or greater than L3+W1 described above. The upper limit of the width W2 may be appropriately determined by the dimension of the radiation detectors 40 or the number of radiation detectors 40, the size of the radiation imaging device 10 (frame body 30), and the like.

In this way, in the radiation imaging device 10 of this modification example, the width W2 of the recess portions 28 is long compared to the embodiment described above, whereby the number of positions capable of gripping the radiation imaging device 10 in each of the first frame 32 and the second frame 34 increase. With this, according to the radiation imaging device 10 of this modification example, the radiation imaging device 10 is easily gripped regardless of the build of various users. According to the radiation imaging device 10 of this modification example, the degree of freedom of the positions to be gripped is improved for different forms of movement of the radiation imaging device 10.

Modification Example 2

Figure 10:
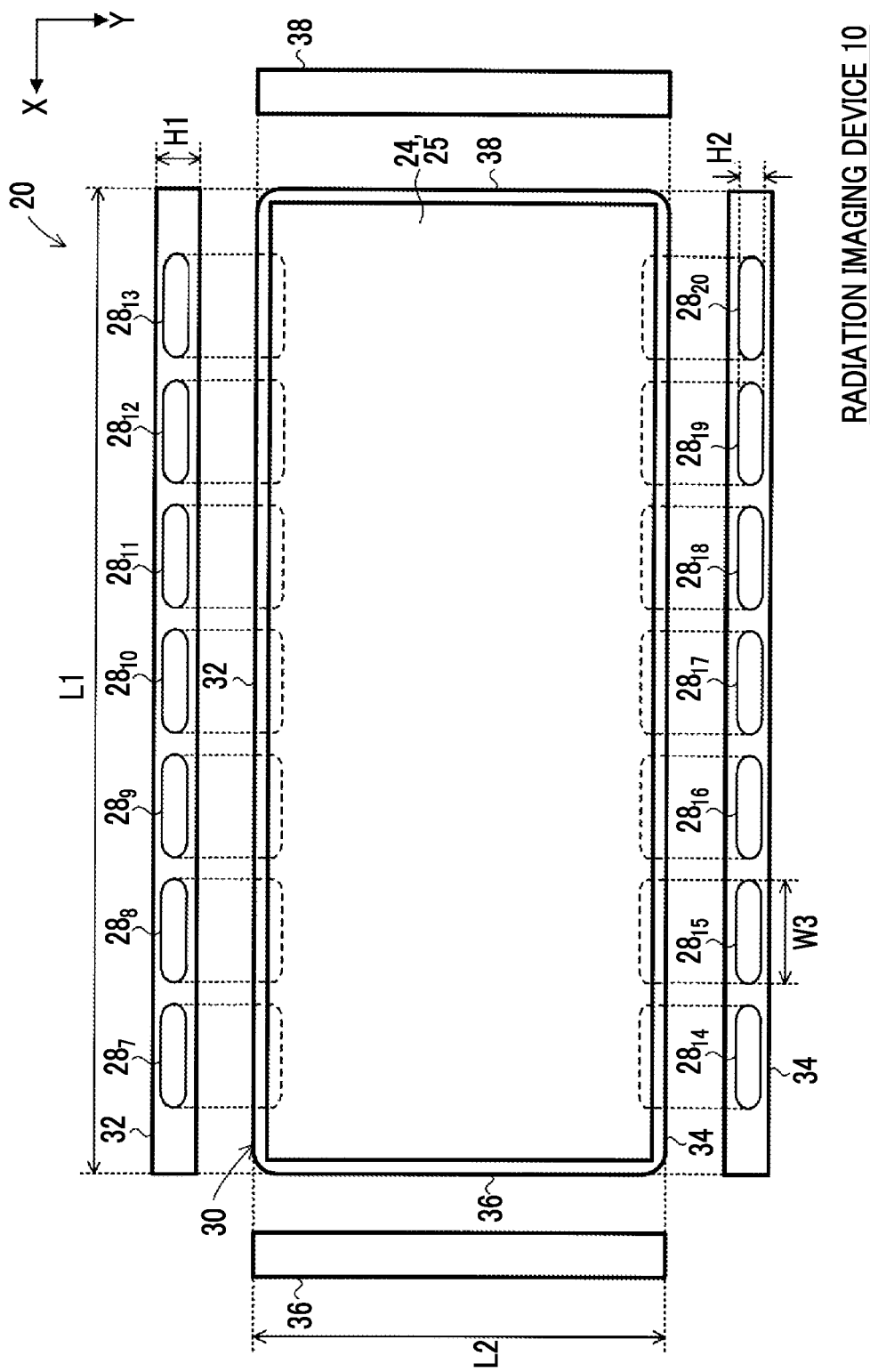
FIG. 10 is a plan view and a side view of an example of a radiation imaging device of Modification Example 2 when viewed from an exposure side of radiation R.

FIG. 10 is a plan view and a side view of an example of a radiation imaging device of this modification example when viewed from an exposure side of radiation R. In FIG. 10, the screw holes 29 are not shown.

In a radiation imaging device 10 of this modification example, in each of the first frame 32 and the second frame 34, the same recess portions 28 as in the embodiment described above are provided such that the radiation imaging device 10 can be gripped at any positions. In this case, since a plurality of recess portions 28 which are narrow in width compared to the recess portions 28 of Modification Example 1 are provided, the strength of the housing 20 is improved compared to Modification Example 1.

As shown in FIG. 10, in the radiation imaging device 10 of this modification example, 14 recess portions $28_7$ to $28_{20}$ are provided. Specifically, the first frame 32 is provided with the recess portions $28_7$ to $28_{13}$, and the second frame 34 is provided with the recess portions $28_{14}$ to $28_{20}$. The recess portions $28_7$ to $28_{13}$ and the recess portions $28_{14}$ to $28_{20}$ are provided at positions facing one another on a one-to-one basis.

The number of recess portions 28 is not limited to this modification example. It is preferable that a plurality of recess portions 28 are provided over a range longer than the interval L3 described above, and may be provided, for example, over the full length of the first frame 32 and the second frame 34 in the longitudinal direction described above.

In the case where the first frame 32 and the second frame 34 are provided with connectors of a power line for supplying power to the radiation imaging device 10 and signal lines, various switches, and the like, it is preferable that the recess portions 28 are not provided at places where the connectors, the switches, and the like are provided.

The width W3 of the recess portions $28_7$ to $28_{20}$ may be equal to or different from the width W1 of the recess portions $28_1$ to $28_4$ of the embodiment described above.

Modification Example 3

Figure 11:
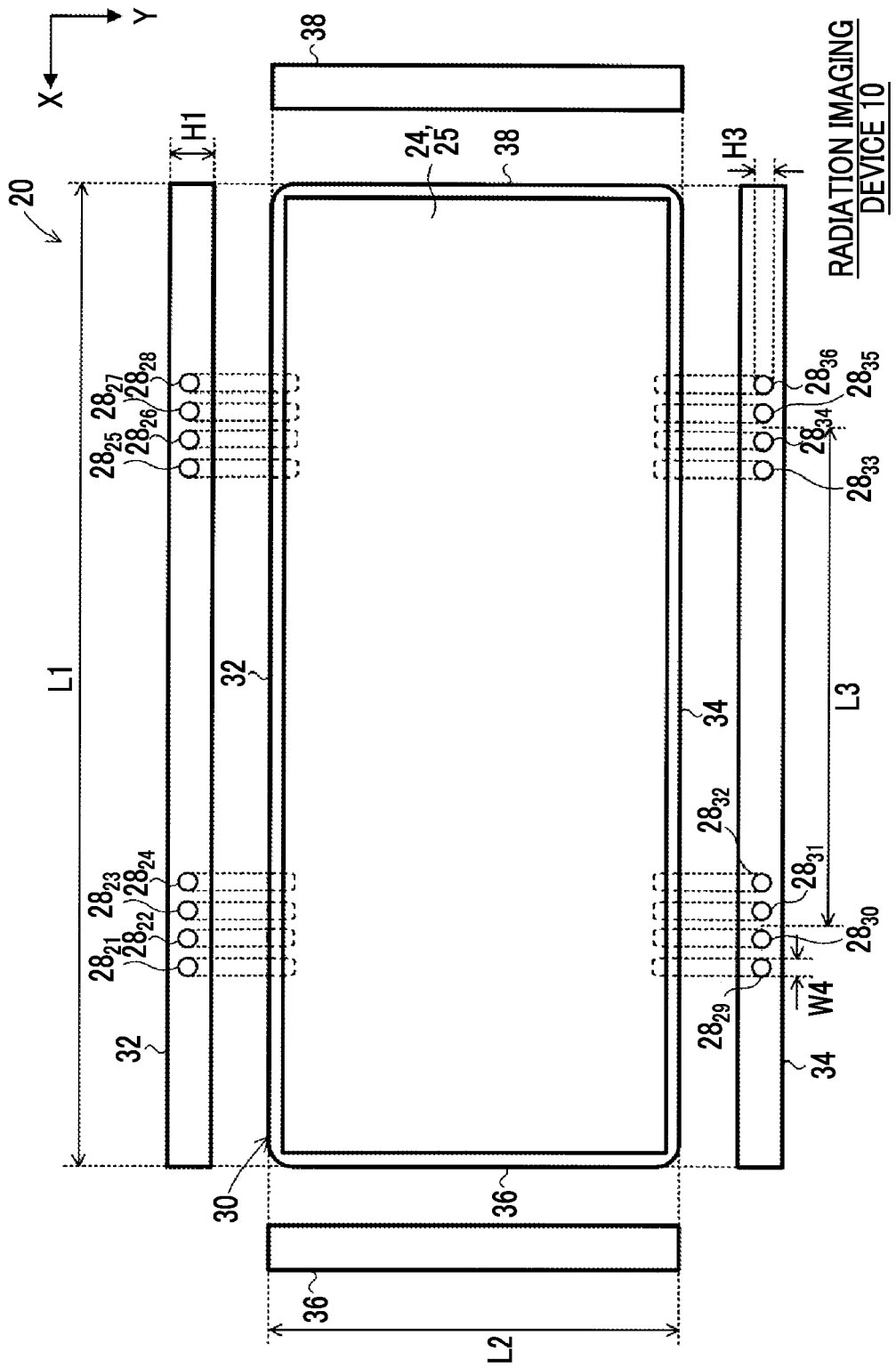
FIG. 11 is a plan view and a side view of an example of a radiation imaging device of Modification Example 3 when viewed from an exposure side of radiation R.

FIG. 11 is a plan view and a side view of an example of a radiation imaging device of this modification example when viewed from an exposure side of radiation R. In FIG. 11, the screw holes 29 are not shown.

In a radiation imaging device 10 of this modification example, a plurality of small recess portions 28 allowing the fingers of the user to be inserted separately are provided.

As shown in FIG. 11, in the radiation imaging device 10 of this modification example, 16 recess portions $28_{21}$ to $28_{36}$ are provided. Specifically, the first frame 32 is provided with the recess portions $28_{21}$ to $28_{28}$, and the second frame 34 is provided with the recess portions $28_{29}$ to $28_{36}$.

The recess portions $28_{21}$ to $28_{24}$ and the recess portions $28_{29}$ to $28_{32}$ are provided at positions facing each other. The recess portions $28_{25}$ to $28_{28}$ and the recess portions $28_{33}$ to $28_{36}$ are provided at positions facing each other.

The recess portions $28_{21}$ to $28_{24}$ of this modification example are provided at positions corresponding to the recess portion $28_1$ of the embodiment described above, and the recess portions $28_{25}$ to $28_{28}$ of this modification example are provided at positions corresponding to the recess portion $28_2$ of the embodiment described above. The recess portions $28_{29}$ to $28_{32}$ of this modification example are provided at positions corresponding to the recess portion $28_3$ of the embodiment described above, and the recess portions $28_{33}$ to $28_{36}$ of this modification example are provided at positions corresponding to the recess portion $28_4$ of the embodiment described above.

The width W4 of the recess portions 28 of this modification example is set to a size allowing one finger of an adult to be sufficiently inserted, and is, for example, a size allowing the test finger defined in JIS C 0920 to be sufficiently inserted. As a specific example, it is preferable that the width W4 is equal to or greater than 13 mm and equal to or less than 30 mm.

In this modification example, although the four recess portions 28 are provided at the four places of each of the first frame 32 and the second frame 34 corresponding to four fingers excluding a thumb, the number of recess portions 28 is not limited to this modification example. For example, the recess portions 28 may be provided over the full length of the first frame 32 and the second frame 34 in the longitudinal direction described above.

Similarly to Modification Example 2, in the case where the first frame 32 and the second frame 34 are provided with connectors of a power line for supplying power to the radiation imaging device 10 and signal lines, various switches, and the like, it is preferable that the recess portions 28 are not provided at places where the connectors, the switches, and the like are provided.

The thickness H3 of the recess portions $28_{21}$ to $28_{36}$ in the thickness direction of the housing 20 may be equal to or different from the length H2 of the recess portions $28_1$ to $28_4$ of the embodiment described above.

Modification Example 4

Figure 12:
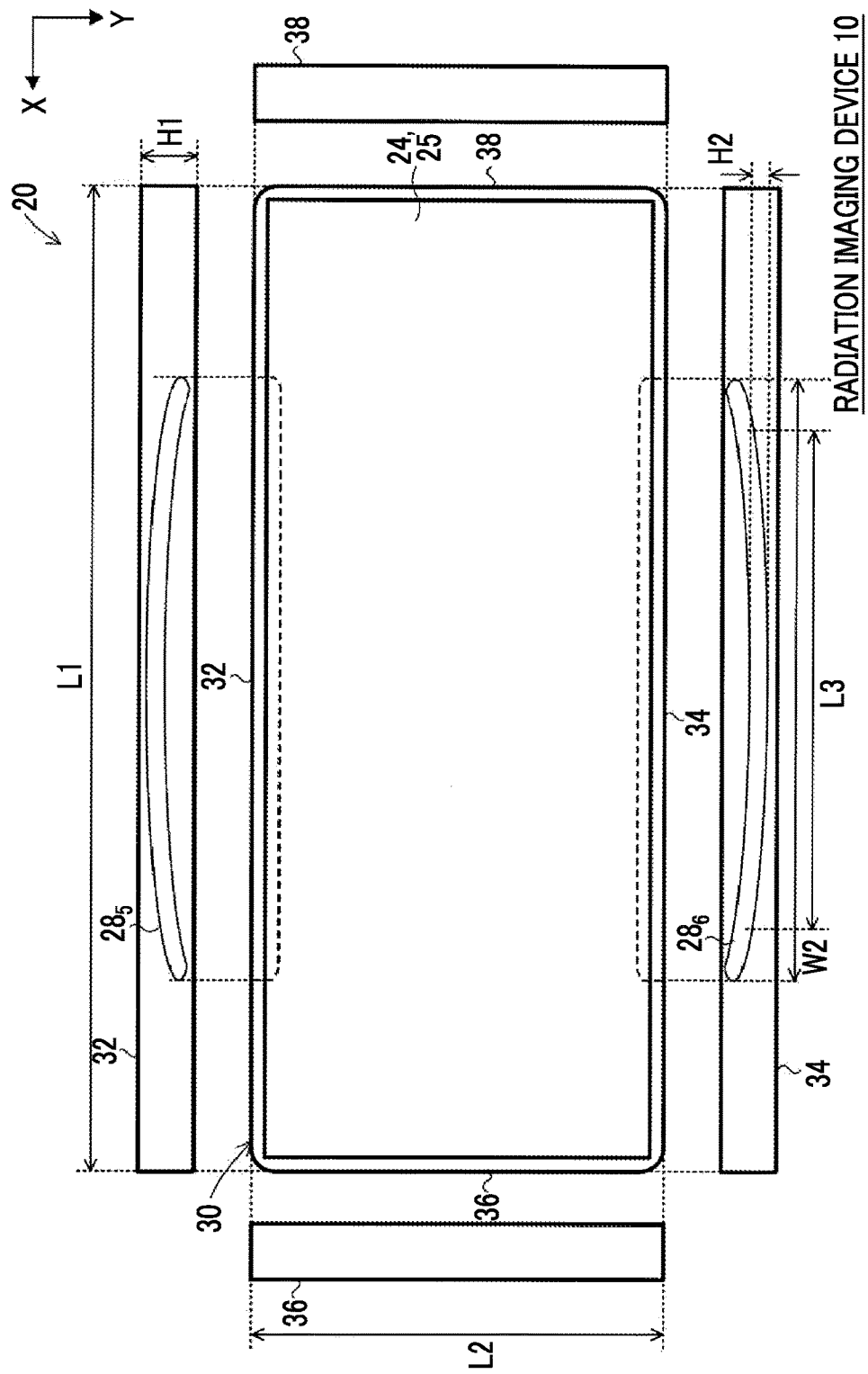
FIG. 12 is a plan view and a side view of an example of a radiation imaging device of Modification Example 4 when viewed from an exposure side of radiation R.

FIG. 12 is a plan view and a side view of an example of a radiation imaging device of this modification example when viewed from an exposure side of radiation R. In FIG. 12, the screw holes 29 are not shown.

In a radiation imaging device 10 of this modification example, the recess portions 28 have an arc shape in side view to extend from the top plate 24 side of the housing 20 toward the back plate 26. In the radiation imaging device 10 shown in FIG. 12, a case where the recess portions $28_5$ and $28_6$ of the radiation imaging device 10 of Modification Example 1 shown in FIG. 9 have an arc shape in side view to extend from the top plate 24 side of the housing 20 toward the back plate 26 is shown.

In this way, in the radiation imaging device 10 of this modification example, the recess portions 28 have an arc shape in side view to extend from the top plate 24 side of the housing 20 toward the back plate 26. For this reason, it is possible to improve ease of gripping the radiation imaging device 10 in the case where the user inserts the fingers of both hands, portions including at least a part of the fingers of both hands and the palm, or the like into the recess portions 28.

Modification Example 5

Figure 13:
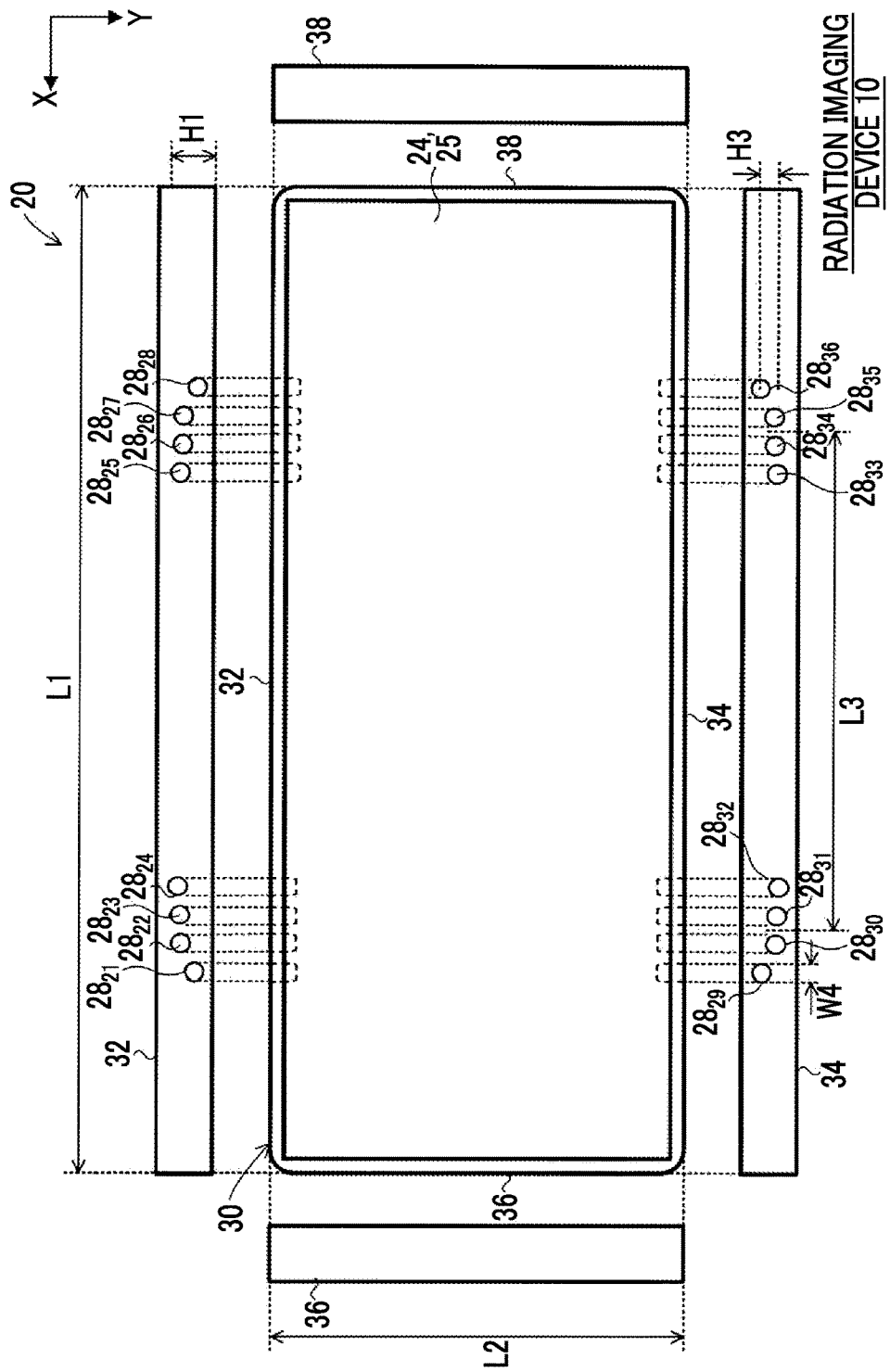
FIG. 13 is a plan view and a side view of an example of a frame body of a radiation imaging device of Modification Example 5 when viewed from an exposure side of radiation R.

FIG. 13 is a plan view and a side view of an example of a radiation imaging device of this modification example when viewed from an exposure side of radiation R. In FIG. 13, the screw holes 29 are not shown.

In the radiation imaging device 10 of this modification example, in each of the first frame 32 and the second frame 34, a plurality of recess portions 28 having the same shape and dimension as Modification Example 3 are arranged in an arc shape in side view to extend from the top plate 24 side of the housing 20 toward the back plate 26 opposite to the top plate 24. In the radiation imaging device 10 shown in FIG. 13, a case where the arrangement positions of the recess portions $28_{21}$ to $28_{28}$ provided in the first frame 32 and the recess portions $28_{29}$ to $28_{35}$ provided in the second frame 34 of the radiation imaging device 10 of Modification Example 3 shown in FIG. 11 have an arc shape in side view to extend from the top plate 24 side of the housing 20 toward the back plate 26 is shown.

As shown in FIG. 13, in the radiation imaging device 10 of this modification example, a plurality of recess portions 28 are arranged in an arc shape in side view to extend from the top plate 24 side of the housing 20 toward the back plate 26, whereby it is possible to improve ease of gripping the radiation imaging device 10 in the case where the user inserts the fingers of both hands into the recess portions 28.

Modification Example 6

Figure 14:
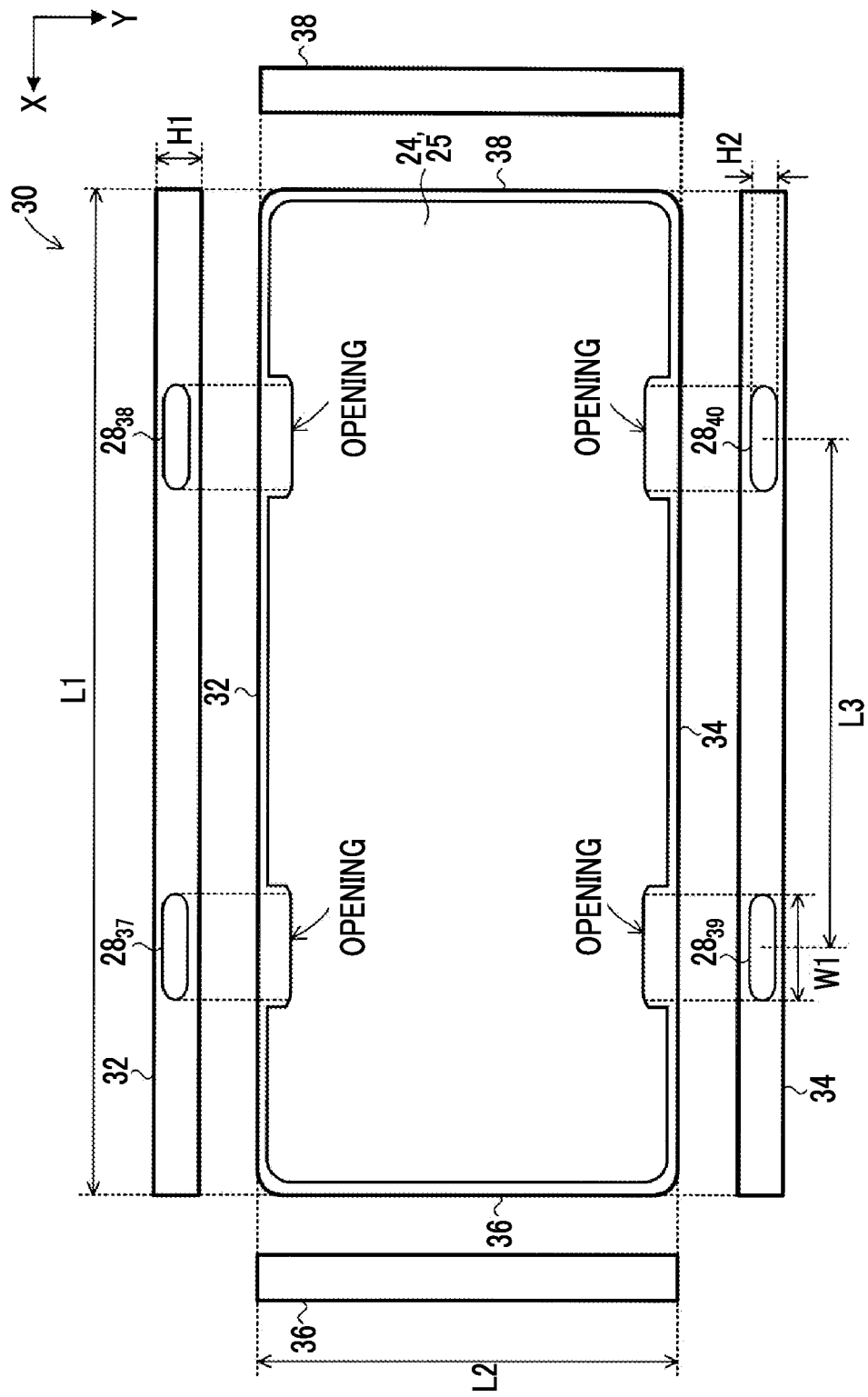
FIG. 14 is a plan view and a side view of an example of a frame body of a radiation imaging device of Modification Example 6 when viewed from an exposure side of radiation R.

FIG. 14 is a plan view and a side view of an example of a frame body 30 of a radiation imaging device 10 of this modification example when viewed from an exposure side of radiation R.

In the radiation imaging device 10 of this modification example, recess portions 28 are provided as through holes where the deepest portion inside a recess is not sealed.

As shown in FIG. 14, in the radiation imaging device 10 of this modification example, four recess portions $28_{37}$ to $28_{40}$ having the substantially same shape and dimension as the recess portions $28_1$ to $28_4$ shown in FIGS. 2 and 3 are provided. However, the recess portions $28_{37}$ to $28_{40}$ of this modification example are through holes where the inside of a recess is open, specifically, as shown in FIG. 14, the deepest portion along the first frame 32 and the second frame 34 are open, unlike the recess portions $28_1$ to $28_4$.

Like the radiation imaging device 10 of this modification example, the recess portions 28 of the embodiment or Modification Examples 1 to 5 described above may not be sealed, or may be through holes having an opening inside the housing 20.

In the radiation imaging device 10 of this modification example, although the screw holes 29 cannot be provided inside the recess portions 28, the imaging stand 13, the imaging stand 15, and the grid 60 (hereinafter, referred to as "imaging stand 13 and the like") can be fixed to the radiation imaging device 10 with no screw holes 29.

Figure 15:
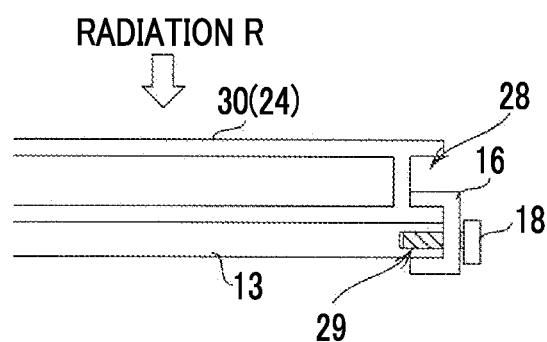
FIG. 15 is an example of a sectional view corresponding to FIG. 6 when a radiation imaging device is fixed to an imaging stand using a recess portion with no screw hole.

Hereinafter, a modification example where the radiation imaging device 10 is fixed to the imaging stand 13 and the like using the recess portions 28 regardless of the presence or absence of the screw holes 29 will be described. FIG. 15 is an example of a sectional view in the case where the radiation imaging device 10 is fixed to the imaging stand 13 using the recess portion 28 with no screw hole 29, and corresponding to FIG. 6. In the example shown in FIG. 15, the screw hole 29 is provided in the sidewall of one end portion of the imaging stand 13. One bent end of the sheet metal 16 is inserted into the recess portion 28, and the end portions of the frame body 30 and the imaging stand 13 are sandwiched by the bent end and the other bent end. In this state, as shown in FIG. 15, the screw 18 is screwed into the screw hole 29 of the imaging stand 13 through the sheet metal 16, whereby the radiation imaging device 10 is fixed to the imaging stand 13. With this form, even if the screws are not screwed into the recess portions 28, the radiation imaging device 10 and the imaging stand 13 and the like can be fixed by the sheet metals 16 and the screws 18.

As described above, each of the radiation imaging devices 10 described above includes the radiation detectors 40 and the housing 20. The radiation imaging device 10 includes a plurality of radiation detectors 40, each of which has the detection surface for detecting a radiation image. The housing 20 includes the top plate 24 and the frame body 30 provided at the edge of the top plate 24, the recess portions 28 being provided in the frame body 30, and accommodates a plurality of radiation detectors 40 in a state where the detection surfaces are aligned in a direction along the surface of the top plate 24.

With this, in the case where the user grips and moves the radiation imaging device 10, the user can insert his/her gripping portions (only the fingers, portions including at least a part of the fingers and the palm, or the like) into the recess portions 28 to grip the radiation imaging device 10. Accordingly, it is possible to easily grip and easily move the radiation imaging device 10, and as a result, user-friendliness is improved.

In general, in the case where a radiation detector is DR, since many electronic components are included, the radiation detector is very heavy compared to a case where a radiation detector is CR. For this reason, in the case where the radiation imaging device 10 is a radiation detector which is DR, it is difficult to move the radiation imaging device 10 compared to a case where a radiation detector is CR. The radiation imaging device 10 including a plurality of radiation detectors further increases in weight.

In contrast, as described above, the recess portions 28 are provided in the frame body 30 which is the housing, whereby the radiation imaging device 10 is easily gripped and moved. If the recess portions 28 are provided, even if a grip which is a protrusion in the housing 20 of the radiation imaging device 10 is not provided, the radiation imaging device 10 is easily gripped or moved. Since the recess portions 28 are provided in each of the first frame 32 and the second frame 34 which are the opposite sides of the housing 20, the radiation imaging device 10 can be moved by two users (first user and second user) in a state of being sandwiched and supported from both sides. From this viewpoint, the radiation imaging device 10 can be easily moved.

Since the recess portions 28 provided in the first frame 32 and the recess portions 28 provided in the second frame 34 are arranged at positions facing each other, from this viewpoint, the moving of the radiation imaging device 10 by the first user and the second user is facilitated. In this configuration, since the application of gripping force to the radiation imaging device 10 is distributed equivalently, it is possible to suppress deformation of the housing 20 at the time of moving of the radiation imaging device 10.

Since the recess portions 28 are provided in each of the first frame 32 and the second frame 34 which becomes the longitudinal sidewalls of the housing 20, from this viewpoint, it is possible to suppress deformation of the housing 20 at the time of moving of the radiation imaging device 10.

In each of the radiation imaging devices 10 described above, since a grip which becomes a protrusion is not provided, in the case of fixing the imaging stand 13 and the like and the radiation imaging device 10, the grip is not obstructive, and fixing is facilitated.

Since each of the radiation imaging devices 10 described above can use the recess portions 28 as fixing portions in the case of being fixed to the imaging stand 13, it is possible to reduce costs of the radiation imaging device 10 compared to a case where an additional fixing portion is provided in the housing 20.

In the radiation imaging device 10, the recess portions 28 can be used n the case of gripping for moving the radiation imaging device 10 and fixing the radiation imaging device 10. With this, it is possible to reduce unnecessary holes and maintain the strength of the housing 20 compared to a case where holes (recess portions) which become gripping portions for moving the radiation imaging device 10 and holes (recess portions) for fixing the radiation imaging device 10 are separately provided as fixing portions.

As shown in FIGS. 1 and 4, each of the radiation imaging devices 10 described above can be used in any of a vertical state and a horizontal state. The radiation imaging device 10 may be used in a state of being fixed to the imaging stand 13 and the like or may be used in a state of being placed on a bed or the like. In this way, since each of the radiation imaging devices 10 described above is compatible with various kinds of imaging, a plurality of types of radiation imaging devices according to the types of imaging or the like need not be provided, and it is possible to achieve reduction in costs.

As described above, according to the respective radiation imaging devices 10 described above, the recess portions 28 are provided in the housing 20, whereby user-friendliness of the radiation imaging device 10 is significantly improved even in a comparatively large device configuration.

Even in the case where a radiation imaging device includes a single radiation detector having a detection surface of a size equal to or greater than a size determined in advance, the same problems as in the radiation imaging device of the related art including a plurality of radiation detectors 40 occur, and user-friendliness is deteriorated. The term "the size of the detection surface" herein used refers to an area. For this reason, it is preferable that a housing of a radiation imaging device which includes a single radiation detector having a detection surface of a size equal to greater than a size determined in advance has the same structure as the housing 20 of each of the radiation imaging devices 10 described above.

Figure 16:
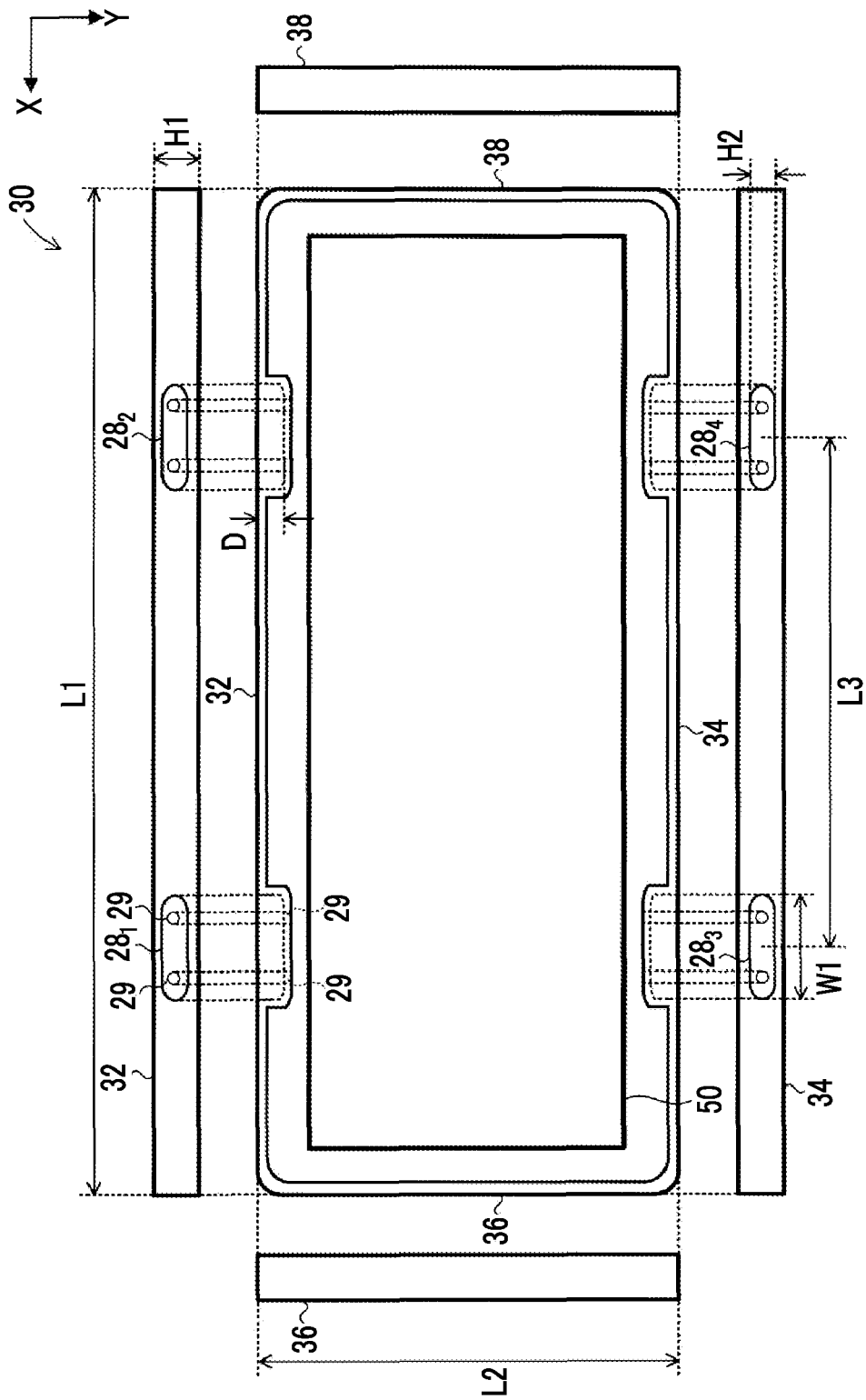
FIG. 16 is a plan view and a side view of a state where a single radiation detector having a detection surface of a size equal to or greater than a size determined in advance is accommodated in the frame body of the radiation imaging device of the embodiment shown in FIG. 3 when viewed from an exposure side of radiation R.

FIG. 16 is a plan view and a side view of a state where a single radiation detector having a detection surface of a size equal to or greater than a size determined in advance is accommodated in the frame body 30 of the radiation imaging device 10 of each of the embodiments shown in FIG. 3 when viewed from an exposure side of radiation R. In this embodiment, the size determined in advance is, for example, a size allowing accommodation in the radiation imaging device 10 having a size and a weight allowing one user to move the radiation imaging device 10. In the radiation imaging device 10 of this embodiment, as a specific example, the size of the detection surface of a radiation detector 50 is equal to the size of the entire detection surface in the case where the three radiation detectors 40 described above are arranged.

In general, in imaging an elongated object as a part of a human body, in the case where the short side of the detection surface of the radiation detector 50 is about 35 cm (14 inches) to about 43 cm (17 inches), and if the ratio between the short side and the long side of the detection surface is equal to or greater than 1.5 and equal to or less than 4, the radiation detector 50 can be applied to so-called spinal imaging. A radiation imaging device 10 which accommodates the radiation detector 50 has a size and dimension such that it is hard for one user to move the radiation imaging device 10.

In this way, in the radiation imaging device 10 which includes the single radiation detector 50 having a detection surface equal to or greater than a size determined in advance, since the recess portions 28 are provided in the frame body 30, and similarly to the respective radiation imaging devices 10 described above, user-friendliness is improved.

In the respective radiation imaging devices 10 described above, as shown in FIG. 5, although a case where a plurality of radiation detectors 40 are arranged in a state where the end portions of the effective imaging regions overlap each other has been described, the radiation detectors 40 may be formed integrally.

Figure 17:
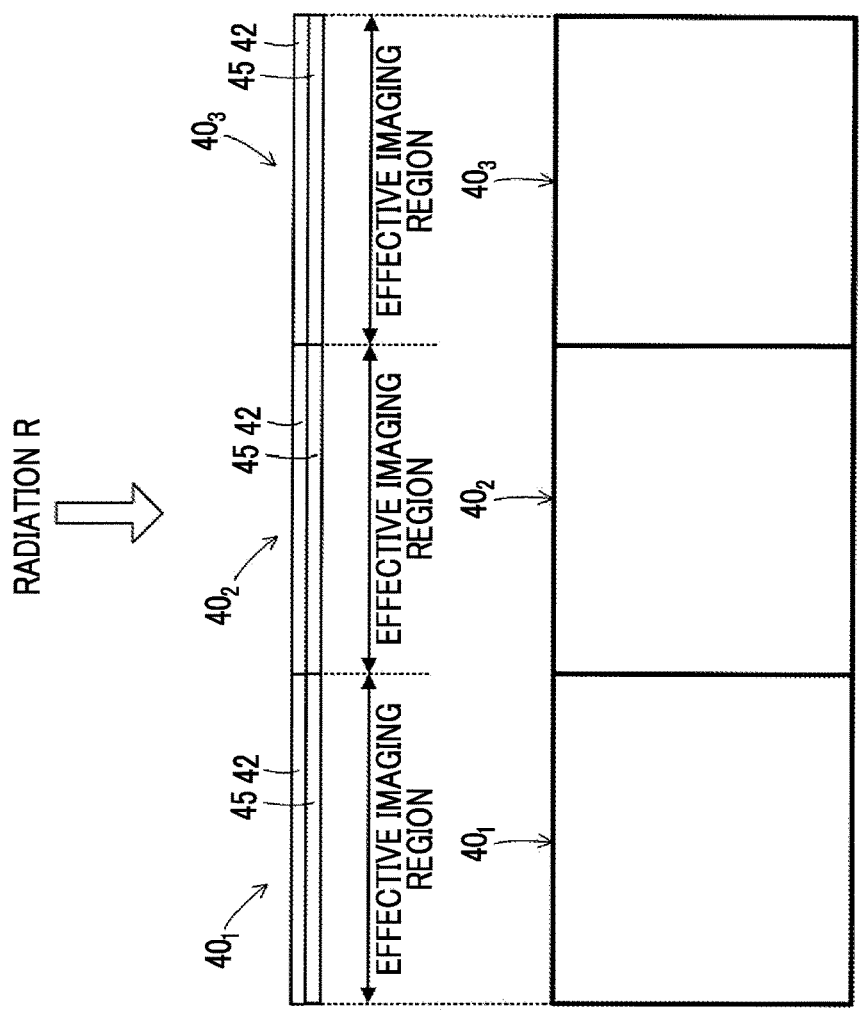
FIG. 17 is a side view and a plan view showing an example of an arrangement state where end portions of effective imaging regions of radiation detectors accommodated inside the housing of the embodiment do not overlap each other.

A plurality of radiation detectors 40 may be arranged in a state where the end portions of the effective imaging regions do not overlap each other. FIG. 17 is a side view and a plan view showing an example of the arrangement state where the end portions of the effective imaging regions of the radiation detectors 40 do not overlap each other. In the case shown in FIG. 17, the end surfaces of the end portions of the radiation detectors 40 are arranged in a state of being in contact with each other or being close to each other. A scintillator 45 of each of the radiation detectors 40 shown in FIG. 17 has the same size as the entire detection surface of the TFT glass substrate 42, unlike the scintillator 44 of each of the radiation detectors 40 shown in FIG. 5. In the example shown in FIG. 17, the end surfaces of the end portions of the radiation detectors 40 are arranged in a state of being in contact with each other or being close to each other with no gap between the effective imaging regions. In this way, in the case where the end surfaces of the end portions of a plurality of radiation detectors 40 are arranged in a state of being in contact with each other or being close to each other, a single scintillator may be provided so as to cover all of the detection surfaces of a plurality of TFT glass substrates 42.

In the recess portions 28, the inside of the recess may be sealed as described above, or may not be sealed. That is, the frame body 30 may have holes or may not have holes. In the case where the inside of the recess is sealed, even if the user inserts the fingers into the recess portions 28, it is possible to prevent the fingertip from coming into contact with the internal radiation detectors 40 or the like. In the case where the inside of the recess is sealed, it is possible to prevent liquids, such as blood, moisture, and chemicals, or foreign substances, such as dust, from entering inside the housing 20. In the case where the inside of the recess is sealed, since the frame body 30 has no holes, the strength of the housing 20 is increased compared to a case where the inside of the recess is not sealed. Even when the inside of the recess in the recess portions 28 is not sealed, that is, even when holes are formed in the frame body 30, it is preferable that an inner wall is provided in the housing 20, or the radiation detectors 40 are covered separately. In this case, when the user inserts the fingers into the recess portion 28, it is possible to prevent the fingertip from coming into contact with the internal radiation detectors 40 or the like, and to prevent foreign substances from entering.

As described above, although it is preferable that the recess portions 28 provided in the first frame 32 and the recess portions 28 provided in the second frame 34 are arranged at positions facing each other, the recess portions 28 provided in the first frame 32 and the recess portions 28 provided in the second frame 34 may not necessarily be provided at positions facing each other.

Although it is preferable that the recess portions 28 are provided in the first frame 32 and the second frame 34 which are the longitudinal sidewalls of the radiation imaging device 10, the recess portions 28 may be provided in the third frame 36 and the fourth frame 38 which are the transverse sidewalls.

The number of recess portions 28 is not limited to that described in the embodiment (including the respective modification examples) described above. However, it is preferable that the radiation imaging device 10 is gripped from both sides by two users (first user and second user) from the viewpoint of efficiency in terms of distribution of gripping force or the number of people necessary for moving, and it is preferable that at least one recess portion 28 is provided in each of the two sidewalls of the frame body 30 facing each other.

A method of fixing the radiation imaging device 10 to the imaging stand 13 and the like is not limited to the methods shown in FIGS. 6 to 8, and 15. The recess portions 28 may be used as fixing portions, and the method is not particularly limited.

As an example, as shown in FIG. 15, even if the screw holes 29 are not provided in the recess portions 28, the radiation imaging device 10 can be fixed to the imaging stand 13 and the like using the recess portion 28 as fixing portions. In this way, the screw holes 29 may not necessarily be provided in the recess portions 28.

The positions of the recess portions 28 may be displayed on the top plate 24 such that the user easily visually recognize the positions of the recess portions 28 from the top surface side. FIG. 18 shows an example of a radiation imaging device 10 in which the positions of the recess portions 28 are displayed on the imaging surface 25 of the top plate 24. In the radiation imaging device 10 shown in FIG. 18, a case where marks 62 representing the positions of the recess portions 28₁ to 28₄ in the radiation imaging device 10 shown in FIG. 2 are displayed on the imaging surface 25 of the top plate 24 is shown.

The shape of the radiation imaging device 10 (housing 20) is not limited to the form of each of the radiation imaging devices 10 described above. As an example, as shown in FIG. 19, the dimension of the back plate 26 side in the case where the frame body 30 is viewed in plan view may be small compared to the top plate 24 (imaging surface 25) side. As shown in a sectional view taken along a cutting line in FIG. 19, even in this case, since the recess portions 28 can be provided in the housing 20, the same effects as the respective radiation imaging devices 10 described above are obtained.

In the respective radiation imaging devices 10 described above, although a case where the radiation imaging device 10 has an elongated rectangular shape in plan view (an oblong shape in plan view) in which the length L1 is longer than the length L2 has been described, the shape of the radiation imaging device 10 is not limited to a rectangular shape. For example, as shown in FIG. 20, a square shape in plan view in which the respective sides of the rectangular shape have the same length L4 may be provided. For example, a case where the radiation detectors 40 are arranged in a square shape, for example, a case where four radiation detectors 40 in total of two radiation detectors 40 in the X-axis direction and two radiation detectors 40 in the Y-axis direction are arranged, or the like, is illustrated as this form. Even in this case, similarly to the respective radiation imaging devices 10 described above, the recess portions 28 are provided, whereby user-friendliness of the radiation imaging device 10 is improved.

The size (dimension) of the radiation imaging device 10 and the recess portion 28 is not limited to the embodiment and the respective modification examples described above. For example, the widths W1 to W3 of the recess portion 28 may be appropriately determined in consideration of the dimension of the radiation detectors 40 or the number of radiation detectors 40, the size of the radiation imaging device 10 (frame body 30), and the like.

The shape of the radiation imaging device 10 (housing 20) may not be a rectangular shape in plan view, and may be for example, a circular shape in plan view and other polygonal shapes.

The number of radiation detectors 40 accommodated in the radiation imaging device 10 may be two or more in the case of accommodating a plurality of radiation detectors 40, and is not particularly limited.

The object may not be a human, and may be living things, such as animals or plants, or other bodies.

Radiation R which is used to capture the radiation image is not particularly limited, and X-rays, y-rays, or the like can be applied.

In addition, the configurations and the operations of the radiation imaging device 10, the housing 20, the frame body 30, and the radiation detector 40 described in this embodiment are an example, and may be changed according to the situation without departing from the gist of the invention.

What is claimed is:

1. A radiation imaging device comprising:
   a plurality of radiation detectors, each of which has a detection surface for detecting a radiation image; and
   a housing which includes a top plate, and a sidewall provided at the edge of the top plate, a recess portion being provided in the sidewall, and accommodates the plurality of radiation detectors in a state where the detection surfaces are aligned in a direction along the surface of the top plate,
   wherein the recess portion receives a mating portion, said mating portion rigidly attaching the housing to an imaging stand.

2. The radiation imaging device according to claim 1, wherein the radiation detectors include a plurality of pixels, each of which includes a sensor unit configured to generate electric charge according to exposed radiation and a switch element configured to read and output the electric charge from the sensor.

3. The radiation imaging device according to claim 1, wherein the inside of a recess in the recess portion is sealed.

4. The radiation imaging device according to claim 1, wherein a plurality of recess portions are provided in the sidewall.

5. The radiation imaging device according to claim 1, wherein the top plate has a rectangular shape, the sidewall includes a pair of sidewalls provided to face each other, and at least one recess portion is provided in each of the pair of sidewalls.

6. The radiation imaging device according to claim 5, wherein the recess portions are provided at facing positions of the pair of sidewalls.

7. The radiation imaging device according to claim 1, wherein the top plate has a rectangular shape, the sidewall includes a pair of sidewalls provided at the edge of the top plate in a longitudinal direction, and the recess portions are provided in the pair of sidewalls.

8. The radiation imaging device according to claim 7, wherein a pair of recess portions are provided in each of a pair of sidewalls provided to face each other.

9. The radiation imaging device according to claim 8, wherein the pair of recess portions in one sidewall and the pair of recess portions in the other sidewall are provided at positions capable of being gripped by both hands of a human.

10. The radiation imaging device according to claim 7, wherein the recess portions are provided in each of a pair of sidewalls provided to face each other in an elongated shape with respect to the direction along the surface of the top plate.

11. The radiation imaging device according to claim 10, wherein the recess portions are provided in an arc shape in plan view to extend from the top plate side toward an opposite side with respect to the direction along the surface of the top plate.

12. The radiation imaging device according to claim 7, wherein a plurality of recess portions are provided in each of a pair of sidewalls provided to face each other with respect to the direction along the surface of the top plate.

13. The radiation imaging device according to claim 12, wherein the recess portions are aligned in an arc shape in plan view to extend from the top plate side toward an opposite side with respect to the direction along the surface of the top plate.

14. The radiation imaging device according to claim 1, wherein the recess portion becomes a fixing portion in the case where the device is fixed to an imaging stand.

15. The radiation imaging device according to claim 14, wherein, in the case where the recess portion becomes a fixing portion and the device is fixed to an imaging stand by a screw, a screw hole into which the screw is screwed is provided inside a recess.

16. The radiation imaging device according to claim 1, wherein the recess portion becomes a fixing portion in the case where an object is imaged using a grid which removes scattered radiation included in radiation transmitted through the object and the device is fixed to the grid.

17. The radiation imaging device according to claim 1, wherein the position of the recess portion is displayed on the top plate.

18. The radiation imaging device according to claim 1, wherein the size of the recess portion is defined by the size of a gripping portion of a human in the case where the human grips the device.

19. The radiation imaging device according to claim 1, wherein the plurality of radiation detectors are accommodated in the housing in a state where the end portions of adjacent radiation detectors overlap each other.

20. The radiation imaging device according to claim 1, wherein the plurality of radiation detectors are formed integrally.

21. The device of claim 1, wherein the recess portion has a bottom surface, and the bottom surface is formed with a through hole for receiving the mating portion, and the mating portion rigidly attaching the housing to the imaging stand is disposed in a longitudinal direction of the recess and attaching the housing to the imaging stand with a supporting metal sheet which also receives the mating portion.

22. A radiation imaging device comprising:
a single radiation detector which has a detection surface for detecting a radiation image, the detection surface having a size equal to or greater than a size determined in advance; and
a housing which includes a top plate, and a sidewall provided at the edge of the top plate, a recess portion being provided in the sidewall, and accommodates the single radiation detector such that the detection surface faces the surface of the top plate,
wherein the recess portion receives a mating portion, said mating portion rigidly attaching the housing to an imaging stand.

* * * * *